US007169615B2

(12) United States Patent
Pai-Paranjape et al.

(10) Patent No.: US 7,169,615 B2
(45) Date of Patent: Jan. 30, 2007

(54) METHOD OF AUTHENTICATING POLYMERS, AUTHENTICATABLE POLYMERS, METHODS OF MAKING AUTHENTICATABLE POLYMERS AND AUTHENTICATABLE ARTICLES, AND ARTICLES MADE THERE FROM

(75) Inventors: Vandita Pai-Paranjape, Evansville, IN (US); Radislav Potyrailo, Niskayuna, NY (US); Philippe Schottland, Evansville, IN (US)

(73) Assignee: General Electric Company, Schenectady, NY (US)

( * ) Notice: Subject to any disclaimer, the term of this patent is extended or adjusted under 35 U.S.C. 154(b) by 380 days.

(21) Appl. No.: 10/723,542

(22) Filed: Nov. 26, 2003

(65) Prior Publication Data

US 2005/0109983 A1    May 26, 2005

(51) Int. Cl.
G01N 21/64 (2006.01)
G01N 31/22 (2006.01)
G06K 7/12 (2006.01)
G06K 19/14 (2006.01)
G11B 7/245 (2006.01)

(52) U.S. Cl. ............... 436/172; 252/408.1; 422/82.08; 428/64.4; 428/64.7; 428/913; 428/916; 359/2; 369/112.01

(58) Field of Classification Search ............ 252/408.1, 252/301.16, 690, 917; 428/1.1, 407, 913, 428/412, 64.4, 64.7, 917; 283/85; 436/56; 359/2; 369/112.01; 422/82.08; 236/164, 236/172

See application file for complete search history.

(56) References Cited

U.S. PATENT DOCUMENTS

| 3,635,895 A | 1/1972 | Kramer |
| 4,001,184 A | 1/1977 | Scott |
| 4,217,438 A | 8/1980 | Brunelle et al. |
| 4,238,524 A | 12/1980 | LaLiberte et al. ............. 427/7 |
| 4,304,899 A | 12/1981 | Mark et al. .................. 528/171 |
| 4,699,510 A | 10/1987 | Alguard |
| 4,813,973 A | 3/1989 | Winnik et al. |
| 5,005,873 A | 4/1991 | West ............................ 283/92 |
| 5,030,697 A | 7/1991 | Hugl et al. |
| 5,118,349 A | 6/1992 | Jalon |
| 5,128,419 A | 7/1992 | Fong et al. |
| 5,137,364 A | 8/1992 | McCarthy |
| 5,142,018 A | 8/1992 | Sakashita et al. |
| 5,151,491 A | 9/1992 | Sakashita et al. |
| 5,201,921 A | 4/1993 | Luttermann et al. ........... 8/506 |
| 5,314,072 A | 5/1994 | Frankel et al. ............. 209/44.1 |
| 5,326,692 A | 7/1994 | Brinkley et al. |
| 5,329,127 A | 7/1994 | Becker et al. ........... 250/459.1 |
| 5,423,432 A | 6/1995 | Krutak et al. ................ 209/577 |
| 5,430,277 A | 7/1995 | Ohno et al. |
| 5,461,136 A | 10/1995 | Krutak et al. ................ 528/289 |
| 5,510,619 A | 4/1996 | Zachmann et al. ..... 250/339.08 |
| 5,530,083 A | 6/1996 | Phelps et al. |
| 5,553,714 A | 9/1996 | Cushman et al. ........... 209/577 |
| 5,573,909 A | 11/1996 | Singer et al. |
| 5,616,674 A | 4/1997 | Michel et al. |
| 5,648,197 A | 7/1997 | Kuroda ................... 430/270.11 |
| 5,703,229 A | 12/1997 | Krutak et al. ................ 540/140 |
| 5,838,451 A | 11/1998 | McCarthy ................... 356/406 |
| 5,925,716 A | 7/1999 | Fu et al. |
| 5,959,065 A | 9/1999 | Heuschen et al. .......... 528/198 |
| 5,966,456 A | 10/1999 | Jones et al. |
| 6,001,953 A | 12/1999 | Davis et al. ................. 528/196 |
| 6,060,577 A | 5/2000 | Davis ......................... 528/196 |
| 6,072,011 A | 6/2000 | Hoover ....................... 525/464 |
| 6,091,563 A | 7/2000 | Thomas, III et al. |
| 6,099,930 A | 8/2000 | Cry et al. .................. 428/64.1 |
| 6,143,839 A | 11/2000 | Webb et al. ................. 525/439 |
| 6,160,787 A | 12/2000 | Marquardt, Jr. et al. |
| 6,162,869 A * | 12/2000 | Sharma et al. .............. 525/170 |
| 6,219,329 B1 | 4/2001 | Kojima et al. |
| 6,251,680 B1 | 6/2001 | Fu et al. |
| 6,296,911 B1 | 10/2001 | Catarineu Guillen ........ 428/29 |
| 6,297,508 B1 | 10/2001 | Barmore et al. |
| 6,355,420 B1 | 3/2002 | Chan |
| 6,364,363 B1 | 4/2002 | Stober et al. |
| 6,365,904 B1 | 4/2002 | Graves |
| 6,380,547 B1 | 4/2002 | Gonzalez et al. |
| 6,402,986 B1 | 6/2002 | Jones, II et al. |
| 6,413,305 B1 | 7/2002 | Mehta et al. |

(Continued)

FOREIGN PATENT DOCUMENTS

DE    1011851    7/1957

(Continued)

OTHER PUBLICATIONS

JP09104679. Publication Date: Apr. 22, 1997. Oxadiazole Derivative and its Production. (Abstract Only).

(Continued)

Primary Examiner—Shean C Wu

(57) ABSTRACT

Disclosed is a method of authenticating that a test polymer is an authenticatable polymer, wherein the authenticatable polymer has an authentication signal and comprises a substrate polymer and an optically variable tag, the optically variable tag having a fluorescence emission whose wavelength and/or intensity change over time, the method comprising subjecting the test polymer to a stimulus sufficient to cause fluorescence of the optically variable tag, determining a test signal from the fluorescence of the test polymer, and authenticating that the test polymer is an authenticatable polymer if the test signal is the same as the authentication signal of the authenticatable polymer.

21 Claims, 12 Drawing Sheets

U.S. PATENT DOCUMENTS

| | | | |
|---|---|---|---|
| 6,475,588 B1 | 11/2002 | Schottland et al. | 428/64.1 |
| 6,475,589 B1 | 11/2002 | Pai-Paranjape et al. | 428/64.1 |
| 6,477,134 B1 | 11/2002 | Stebbings et al. | 369/272 |
| 6,514,617 B1 | 2/2003 | Hubbard et al. | |
| 6,537,636 B1 | 3/2003 | Wisnudel et al. | 428/64.1 |
| 6,559,270 B1 | 5/2003 | Siclovan et al. | |
| 6,589,626 B2 | 7/2003 | Selinfreund et al. | 428/64.1 |
| 6,607,814 B2 | 8/2003 | Pickett et al. | 428/212 |
| 6,610,351 B2 | 8/2003 | Shchegolikhin et al. | |
| 6,638,593 B2 | 10/2003 | Seiinfreund et al. | |
| 6,706,218 B2 | 3/2004 | Lucht et al. | |
| 6,707,539 B2 | 3/2004 | Seiinfreund et al. | |
| 7,094,364 B2 * | 8/2006 | Potyrailo et al. | 252/408.1 |
| 2002/0142236 A1 | 10/2002 | Iwasaki et al. | |
| 2002/0149003 A1 | 10/2002 | Lucht et al. | 252/408.1 |
| 2002/0191517 A1 | 12/2002 | Honda et al. | 369/53.29 |
| 2003/0012562 A1 | 1/2003 | Lawandy et al. | |
| 2003/0021998 A1 | 1/2003 | Hubbard et al. | |
| 2003/0052305 A1 | 3/2003 | Coates et al. | |
| 2003/0152774 A1 | 8/2003 | Cradic et al. | 428/412 |
| 2003/0191952 A1 | 10/2003 | Anderson et al. | |
| 2005/0109983 A1 | 5/2005 | Pai-Paranjape et al. | |
| 2005/0110978 A1 | 5/2005 | Potyrailo et al. | |
| 2005/0111342 A1 | 5/2005 | Morris et al. | |
| 2005/0112768 A1 | 5/2005 | Evans et al. | |

FOREIGN PATENT DOCUMENTS

| | | |
|---|---|---|
| DE | 102 48 870 A1 | 4/2004 |
| EP | 0 121 261 | 10/1984 |
| EP | 0 181 228 B1 | 7/1985 |
| EP | 0438225 A1 | 7/1991 |
| EP | 0 608 078 A1 | 1/1994 |
| EP | 0 648 798 A1 | 4/1994 |
| EP | 0 625 766 B1 | 5/1994 |
| EP | 0 698 419 B1 | 6/1994 |
| EP | 0648798 A1 | 4/1995 |
| EP | 0438225 B1 | 10/1996 |
| EP | 1 220 165 A3 | 10/2001 |
| GB | 266455 | 2/1924 |
| GB | 1 270 965 | 11/1969 |
| GB | 1 487 967 | 10/1977 |
| GB | 2264558 A | 9/1993 |
| GB | 2330408 A | 4/1999 |
| GB | 2 345 879 A | 7/2000 |
| JP | 3214438 | 7/1991 |
| JP | 08-096508 | 4/1996 |
| JP | 08-138268 | 5/1996 |
| WO | WO 98/31011 | 7/1998 |
| WO | WO 00/14736 | 3/2000 |
| WO | WO 00/77104 A1 | 12/2000 |
| WO | WO 01/20591 A1 | 3/2001 |
| WO | WO 02/03106 A2 | 1/2002 |
| WO | WO 02/03386 A2 | 1/2002 |
| WO | WO 03/087888 A2 | 10/2003 |
| WO | WO 03/105075 A1 | 12/2003 |

OTHER PUBLICATIONS

International Search Report for International application No. PCT/US2004/039467. Mailed May 10, 2005.

International Search Report for International application No. PCT/US2004/041349. Mailed Apr. 11, 2005.

International Search Report for International application No. PCT/US2004/037687. Mailed May 12, 2005.

International Search Report for International application No. PCT/US2004/038667. Mailed Jun. 2, 2005.

Cantrell, et al. "The SLIM Spectrometer" Anal. Chem. 2003, 75, 27-35.

M.G. Baron et al., Temperature Sensing Using Reversible Thermochromic Polymeric Films; Sensors And Actuators B 90 (2003) 271-275.

* cited by examiner

METHOD OF AUTHENTICATING
POLYMERS, AUTHENTICATABLE
POLYMERS, METHODS OF MAKING
AUTHENTICATABLE POLYMERS AND
AUTHENTICATABLE ARTICLES, AND
ARTICLES MADE THERE FROM

BACKGROUND OF INVENTION

The inventions relate to authentication technology for polymer based articles, particularly to methods of authenticating polymer based articles, methods of facilitating such authentication, and methods of making articles capable of authentication. The invention particularly relates to nondestructive authentication technology for use in data storage media made of polycarbonate such as compact disks (CDs) and digital versatile disks (DVDs).

Data storage media or optical storage media such as CDs and DVDs traditionally contain information such as machine-readable code, audio, video, text, and/or graphics. Data storage media often include one or more substrates made of polymers such as polycarbonate.

A major problem confronting the various makers and users of data storage media is the unauthorized reproduction or copying of information by unauthorized manufacturers, sellers and/or users. Such unauthorized reproduction or duplication of data storage media is often referred to as piracy and can occur in a variety of ways, including consumer level piracy at the point of end use as well as whole sale duplication of data, substrate and anti-piracy information at the commercial level. Regardless of the manner, piracy of data storage media deprives legitimate software and entertainment content providers and original electronic equipment manufacturers significant revenue and profit.

Attempts to stop piracy at the consumer level have included the placement of electronic anti-piracy signals on information carrying substrates along with the information sought to be protected. The machine readers and players of such data storage media are configured to require the identification of such anti-piracy signals prior to allowing access to the desired information. Theoretically, consumer level duplications are unable to reproduce these electronic anti-piracy signals on unauthorized copies and hence result in duplicates and copies that are unusable.

However, numerous technologies to thwart such consumer level anti-piracy technologies have been and continue to be developed. Moreover, commercial level duplications have evolved to the point that unauthorized duplicates now contain the original electronic anti-piracy circuit, code, etc. For example, commercial level duplication methods include pit copying, radio frequency (RF) copying, "bit to bit" copying and other mirror image copying techniques which result in the placement of the anti-piracy signal on the information carrying substrate of the duplicate along with the information sought to be protected. Other technologies commonly used by hackers include the modification of the computer code in order to remove anti-piracy (also referred to as copy-protection or copy-proofing) features and enable unlimited access to the data.

One anti-piracy technology aimed at combating these more sophisticated consumer and commercial level reproduction and copying practices involves the placement of 'tags' or authentication markers in substrates used in the construction of data storage media. Such tags or authentication markers can be detected at one or more points along the data storage media manufacturing or distribution chain or by the end use reader or player used to access the data on a particular CD or DVD.

For example, in Cyr et al., U.S. Pat. No. 6,099,930, tagging materials are placed in materials such as digital compact discs. A near-infrared fluorophore is incorporated into the compact disc via coating, admixing, blending or copolymerization. Fluorescence is detectable when the fluorophore is exposed to electromagnetic radiation having a wavelength ranging from 670 to 1100 nanometers.

Hubbard et al., U.S. Pat. No. 6,514,617 discloses a polymer comprising a tagging material wherein the tagging material comprises an organic fluorophore dye, an inorganic fluorophore, an organometallic fluorophore, a semi-conducting luminescent nanoparticle, or combination thereof, wherein the tagging material has a temperature stability of at least about 350 degrees C. and is present in a sufficient quantity such that the tagging material is detectable via a spectrofluorometer at an excitation wavelength from about 100 nanometers to about 1100 nanometers.

WO 00/14736 relies on one or more intrinsic physical or chemical characteristics of the substrate materials to distinguish unauthorized duplications of information-carrying substrates. Such anti-piracy characteristics may be based on performance characteristics such as (for example in the case of an optical disc) the weight and/or density of the disc; the spin rate of the disc; the acceleration and deceleration of the disc; the inertia of the disc; the spectral characteristics such as reflectance of the disc; the optical characteristics such as light transmittance of the disc; the water absorption and dimensional stability of the disc; the data transfer rate of the disc; and the degree of wobble of the disc, or combinations of such characteristics.

Catarineu Guillén, U.S. Pat. No. 6,296,911 discloses a method for obtaining the chromatic variation of objects in response to external stimuli, the method comprising the incorporation in the desired objects of various pigments having combined effects comprising a luminescent pigment, a thermochromic pigment permitting the change in the color according to the temperature and/or a hygroscopic pigment that will provoke a variation in the chromatic characteristics according to humidity.

U.S. Pat. No. 5,329,127 discloses a method of identifying different plastics, wherein each plastic is provided with a plurality of fluorescence dyes which differ in terms of their emission frequencies and/or in terms of the duration of their fluorescence, so that a fluorescence pattern, which is distinguished by the duration of the fluorescence and/or by the frequencies occurring, can unambiguously be assigned to each plastic.

However, the ability of unauthorized manufacturers, sellers, and/or users of data storage media to circumvent such practices continues to grow with increasingly sophisticated practices. For example, unauthorized manufacturers of data storage media are known to illegally obtain legitimately manufactured-tagged substrates for the purposes of making unauthorized reproductions. Moreover, the high profitability of piracy has enabled some unauthorized manufacturers and their suppliers to reverse engineer tagged substrate materials for the purpose of identifying previously unknown tags and producing similarly tagged data media storage substrate.

There is therefore a need to find methods of tagging and authenticating data storage media substrates that are currently unknown and/or unavailable to unauthorized manufacturers, sellers, and/or users of data storage media. In particular, it would be desirable to find authentication markers or combinations of authentication markers for use in data storage media substrates that are difficult to obtain, reproduce, use, and/or find for the purposes of authenticating data storage media substrates and data storage media.

BRIEF DESCRIPTION OF THE INVENTION

Disclosed herein are embodiments for a method of authenticating a polymer or an article, authenticatable polymers, methods of making authenticatable polymers and articles, and authenticatable articles made from the disclosed methods.

In one embodiment, a method of authenticating that a test polymer is an authenticatable polymer is disclosed, wherein the authenticatable polymer has an authentication signal and comprises a substrate polymer and an optically variable tag, the optically variable tag having a fluorescence emission whose wavelength and/or intensity change over time, the method comprising subjecting the test polymer to a stimulus sufficient to cause fluorescence of the optically variable tag, determining a test signal from the fluorescence of the test polymer, and authenticating that the test polymer is an authenticatable polymer if the test signal is the same as the authentication signal of the authenticatable polymer.

In another embodiment an authenticatable polymer disclosed, comprising a substrate polymer and an optically variable tag having a fluorescence emission whose wavelength and/or intensity changes over time.

Also disclosed is a method of making an authenticatable polymer, comprising incorporating together a substrate polymer and an optically variable tag to make an authenticatable polymer, wherein the optically variable tag has a fluorescence emission having a wavelength and/or intensity change over time.

Finally, a method of making an authenticatable article is disclosed, the method comprising providing the disclosed authenticatable polymer, and forming an authenticatable article from the authenticatable polymer.

BRIEF DESCRIPTION OF THE DRAWINGS

Referring now to the figures, which are exemplary, not limiting.

DETAILED DESCRIPTION

Figure 1:
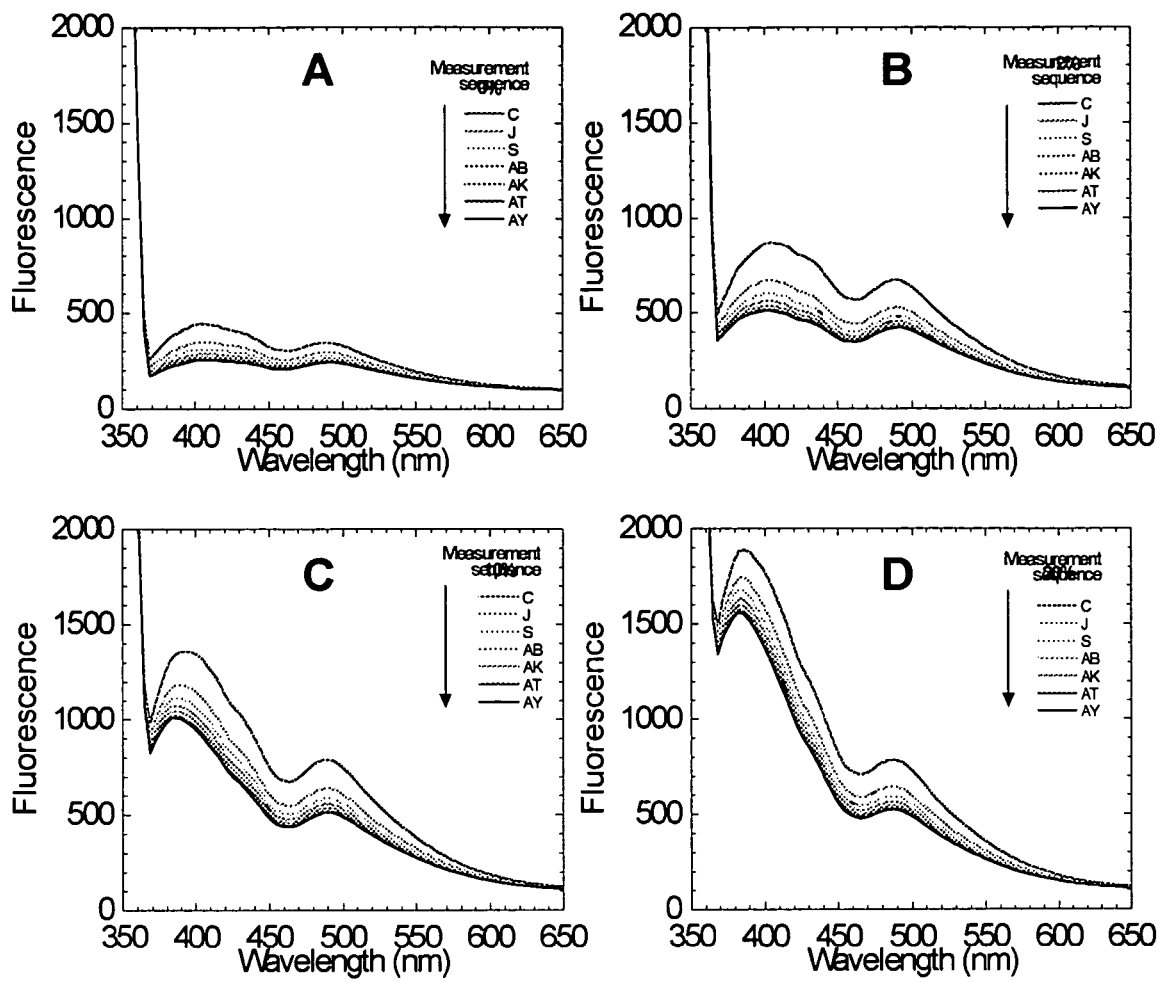
FIGS. 1A, 1B, 1C, and 1D graphically illustrate the effect of concentration upon the time-dependent fluorescence spectra of the fluorescent tag tert-butyl phenyl oxadiazole incorporated into polycarbonate.

Disclosed herein are authenticatable polymers and methods of facilitating the authentication of polymer-based articles as well as method of making authenticatable polymers that can be used to make authenticatable articles. The use of the authenticatable polymers disclosed herein in various polymer based articles allows for one or more parties at any point along the manufacturing chain, distribution chain, point of sale or point of use of the article to confirm or identify the presence or absence of the authenticatable polymer.

The authenticatable polymers disclosed herein are used as a reference standard with respect to the methods of authenticating disclosed therein. The disclosed method of authenticating test polymers provides valuable information. For example, the identification of a test polymer as an authenticatable polymer can provide one or more pieces of information such as the source of the test polymer or test article, the composition of the test polymer, whether the test polymer or test article is an unauthorized reproduction or duplication, the serial number (or lot number) of the test polymer, the date of manufacture, and the like. In some instances, a failure to authenticate that a test polymer is an authenticatable polymer will serve as proof of unauthorized duplication or copying. The authenticatable polymers disclosed herein may be used to form authenticatable articles. The disclosed methods of authenticating may be used to authenticate either polymers or articles.

The disclosed authenticatable polymers will generally comprise a substrate polymer and an optically variable tag.

Some possible examples of suitable polymers which can be utilized as the substrate polymer include, but are not limited to, amorphous, crystalline and semi-crystalline thermoplastic materials: polyvinyl chloride, polyolefins (including, but not limited to, linear and cyclic polyolefins and including polyethylene, chlorinated polyethylene, polypropylene, and the like), polyesters (including, but not limited to, polyethylene terephthalate, polybutylene terephthalate, polycyclohexylmethylene terephthalate, and the like), polyamides, polysulfones (including, but not limited to, hydrogenated polysulfones, and the like), polyimides, polyether imides, polyether sulfones, polyphenylene sulfides, polyether ketones, polyether ether ketones, ABS resins, polystyrenes (including, but not limited to, hydrogenated polystyrenes, syndiotactic and atactic polystyrenes, polycyclohexyl ethylene, styrene-co-acrylonitrile, styrene-co-maleic anhydride, and the like), polybutadiene, polyacrylates (including, but not limited to, polymethylmethacrylate, methyl methacrylate-polyimide copolymers, and the like), polyacrylonitrile, polyacetals, polycarbonates, polyphenylene ethers (including, but not limited to, those derived from 2,6-dimethylphenol and copolymers with 2,3,6-trimethylphenol, and the like), ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, Teflons, as well as thermosetting resins such as epoxy, phenolic, alkyds, polyester, polyimide, polyurethane, mineral filled silicone, bis-maleimides, cyanate esters, vinyl, and benzocyclobutene resins, in addition to blends, copolymers, mixtures, reaction products and composites comprising a of the foregoing plastics.

As used herein, the terms "polycarbonate", "polycarbonate composition", and "composition comprising aromatic carbonate chain units" includes compositions having structural units of the formula (I):

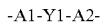

in which at least about 60 percent of the total number of R1 groups are aromatic organic radicals and the balance thereof are aliphatic, alicyclic, or aromatic radicals. Preferably, R1 is an aromatic organic radical and, more preferably, a radical of the formula (II):

-A1-Y1-A2- wherein each of A1 and A2 is a monocyclic divalent aryl radical and Y1 is a bridging radical having one or two atoms which separate A1 from A2. In an exemplary embodiment, one atom separates A1 from A2. Illustrative, non-limiting examples of radicals of this type are —O—, —S—, —S(O)—, —S(O)—, —C(O)—, methylene, cyclohexylmethylene, 2-[2,2,1]-bicycloheptylidene, ethylidene, isopropylidene, neopentylidene, cyclohexylidene, cyclopentadecylidene, cyclododecylidene, and adamantylidene. The bridging radical Y1 can be a hydrocarbon group or a saturated hydrocarbon group such as methylene, cyclohexylidene or isopropylidene.

Polycarbonates can be produced by the interfacial reaction of dihydroxy compounds in which only one atom separates A1 and A2. As used herein, the term "dihydroxy compound" includes, for example, bisphenol compounds having general formula (III) as follows:

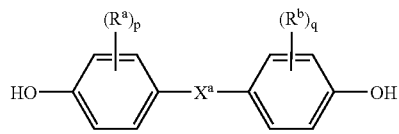

wherein Ra and Rb each represent a halogen atom or a monovalent hydrocarbon group and may be the same or different; p and q are each independently integers from 0 to 4; and Xa represents one of the groups of formula (IV):

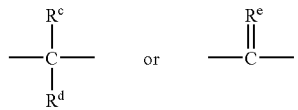

wherein Rc and Rd each independently represent a hydrogen atom or a monovalent linear or cyclic hydrocarbon group and Re is a divalent hydrocarbon group.

Some illustrative, non-limiting examples of suitable dihydroxy compounds include dihydric phenols and the dihydroxy-substituted aromatic hydrocarbons disclosed by name or formula (generic or specific) in U.S. Pat. No. 4,217,438. A nonexclusive list of specific examples of the types of bisphenol compounds that may be represented by formula (III) includes the following: 1,1-bis(4-hydroxyphenyl)methane; 1,1-bis(4-hydroxyphenyl)ethane; 2,2-bis(4-hydroxyphenyl)propane (hereinafter "bisphenol A" or "BPA"); 2,2-bis(4-hydroxyphenyl)butane; 2,2-bis(4-hydroxyphenyl)octane; 1,1-bis(4-hydroxyphenyl)propane; 1,1-bis(4-hydroxyphenyl)n-butane; bis(4-hydroxyphenyl)phenylmethane; 2,2-bis(4-hydroxy-1-methylphenyl)propane; 1,1-bis(4-hydroxy-t-butylphenyl)propane; bis(hydroxyaryl)alkanes such as 2,2-bis(4-hydroxy-3-bromophenyl)propane; 1,1-bis(4-hydroxyphenyl)cyclopentane; and bis(hydroxyaryl)cycloalkanes such as 1,1-bis(4-hydroxyphenyl)cyclohexane; and the like as well as combinations comprising the foregoing.

It is also possible to employ two or more different dihydric phenols or a copolymer of a dihydric phenol with a glycol or with a hydroxy- or acid-terminated polyester or with a dibasic acid or with a hydroxy acid in the event a carbonate copolymer rather than a homopolymer is desired for use. Polyarylates and polyester-carbonate resins or their blends can also be employed. Branched polycarbonates are also useful, as well as blends of linear polycarbonate and a branched polycarbonate. The branched polycarbonates may be prepared by adding a branching agent during polymerization.

These branching agents are well known and may comprise polyfunctional organic compounds containing at least three functional groups which may be hydroxyl, carboxyl, carboxylic anhydride, haloformyl and mixtures comprising a of the foregoing. Specific examples include trimellitic acid, trimellitic anhydride, trimellitic trichloride, tris-p-hydroxy phenyl ethane, isatin-bis-phenol, tris-phenol TC (1,3, 5-tris((p-hydroxyphenyl)isopropyl)benzene), tris-phenol PA (4(4(1,1-bis(p-hydroxyphenyl)-ethyl) alpha,alpha-di methyl benzyl)phenol), 4-chloroformyl phthalic anhydride, trimesic acid and benzophenone tetracarboxylic acid, and the like. The branching agents may be added at a level of about 0.05 to about 2.0 weight percent. Branching agents and procedures for making branched polycarbonates are described in U.S. Pat. Nos. 3,635,895 and 4,001,184. All types of polycarbonate end groups are herein contemplated.

In one embodiment, the polymer will be a polycarbonate based on bisphenol A, in which each of A1 and A2 is p-phenylene and Y1 is isopropylidene. In one embodiment, the average molecular weight of the polycarbonate is about 5,000 to about 100,000. In another exemplary embodiment, the average molecular weight of a polycarbonate used as the polymer will be about 10,000 to about 65,000, while in another exemplary embodiment, a polycarbonate used as the polymer will have an average molecular weight of about 15,000 to about 35,000.

In monitoring and evaluating polycarbonate synthesis, it is of particular interest to determine the concentration of Fries product present in the polycarbonate. Polycarbonates produced by a melt process or activated carbonate melt process such of those listed in U.S. Pat. Nos. 5,151,491 and 5,142,018 typically contain a significantly higher concentration of Fries product. As noted, the generation of significant Fries product can lead to polymer branching, resulting in uncontrollable melt behavior. As used herein, the terms "Fries" and "Fries product" denote a repeating unit in polycarbonate having the formula (V):

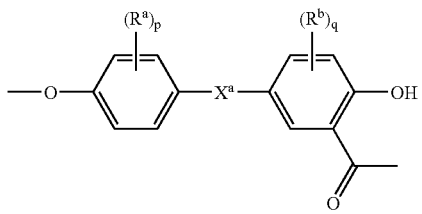

wherein Xa is a bivalent radical as described in connection with Formula (III) described above.

Polycarbonate compositions suitable for use as the substrate polymer may also include various additives ordinarily incorporated in resin compositions of this type. Such additives are, for example, fillers or reinforcing agents; heat stabilizers; antioxidants; light stabilizers; plasticizers; antistatic agents; mold releasing agents; additional resins; blowing agents; and the like, as well as combinations comprising a of the foregoing additives. Examples of fillers or reinforcing agents include glass fibers, asbestos, carbon fibers, silica, talc and calcium carbonate. Examples of heat stabilizers include triphenyl phosphite, tris-(2,6-dimethylphenyl)phosphite, tris-(mixed mono- and di-nonylphenyl)phosphite, dimethylbenene phosphonate and trimethyl phosphate. Examples of antioxidants include octadecyl-3-(3,5-di-tert-butyl-4-hydroxyphenyl)propionate, and pentaerythrityl-tetrakis[3-(3,5-di-tert-butyl-4-hydroxyphenyl)propionate]. Examples of light stabilizers include 2-(2-hydroxy-5-methylphenyl)benzotriazole, 2-(2-hydroxy-5-tert-octylphenyl)-benzotriazole and 2-hydroxy-4-n-octoxy benzophenone. Examples of plasticizers include dioctyl-4,5-epoxy-hexahydrophthalate, tris-(octoxycarbonylethyl)isocyanurate, tristearin and epoxidized soybean oil. Examples of the antistatic agent include glycerol monostearate, sodium stearyl sulfonate, and sodium dodecylbenzenesulfonate. Examples of mold releasing agents include stearyl stearate, beeswax, montan wax and paraffin wax. Examples of other resins include but are not limited to polypropylene, polystyrene, polymethyl methacrylate, and polyphenylene oxide. Combinations of any of the foregoing additives may be used. Such additives may be mixed at a suitable time during the mixing of the components for forming the composition.

The term 'optically variable tag' generally refers to compounds that have a fluorescence emission that changes in fluorescence intensity and/or wavelength as a function of time. The authenticatable polymers have an authenticating signal that is based on the variable fluorescence emission of the optically variable tags. In one embodiment, the authenticatable polymers disclosed herein may be designed to be evaluated several times, i.e., the authenticating signal is repeatable, while in other embodiments the authenticating signal may be capable of evaluation only once due to the use of optically variable tags that degrade after one or more authentication sequences. In one exemplary embodiment, the authenticatable polymer will comprise an optically variable tag that can be authenticated multiple times, i.e., for example, at various points in a distribution or supply chain.

In one embodiment, the authenticatable polymers disclosed herein may be identified by an authenticating signal that is the shift of the characteristic wavelength of the fluorescence emission of the optically variable tag, i.e., a variable fluorescence peak position during the time of authentication. The substrate polymers used in the authenticatable polymers do not demonstrate any wavelength shift in the absence of the optically variable tags. In one embodiment, the optically variable tags have a fluorescence emission that is not be visible to the unaided human eye because the emission is not in the visible range or is hidden (e.g. hidden behind the "natural" fluorescence emission of polycarbonate). In one further embodiment, the presence of the optically variable tags in the authenticatable polymers or articles could not be detected visually using a standard UV lamp.

The optically variable tags have a fluorescence emission whose wavelength and intensity change over time. In one embodiment, the optically variable tag will have a fluorescence emission characterized by a first peak position at an initial time and a second peak position at a second, later time. The second peak position may generally be identified in terms of the shift from the first peak position. In one embodiment, the first peak position of the fluorescence emission will be at about 160 to about 1100 nm, while the other peak position of the fluorescence emission will be shifted from the first peak by about 2 to about 300 nm. In one exemplary embodiment, a first peak will be at about 250 to about 750 nm, while the second peak may be shifted by about 5 to about 200 nm. In another exemplary embodiment, the first peak will be at about 300 to about 700 nm, while the second peak will be shifted by about 10 to about 100 nm.

In another embodiment, the authenticatable polymers disclosed herein may be identified via an authenticating signal that is the predetermined change of the fluorescence ratio of emission intensities at two or more pre-selected wavelengths. These pre-selected wavelengths are selected so that the fluorescence ratio of a polymer without the optically variable tags changes in one direction, normally a decrease, while the fluorescence ratio of an authenticatable polymer comprising the optically variable tags changes in the opposite direction, i.e., normally an increase.

Pre-selected wavelengths are preferably selected as the maximum fluorescence emission. Typically, the first pre-selected wavelength corresponds to the first peak emission while the second pre-selected wavelength corresponds to the second peak emission. In one embodiment, the pre-selected wavelengths will be about 160 to 1100 nm. In one exemplary embodiment, one pre-selected wavelength will be selected at a wavelength within +/−10 nm of the maximum peak emission. In another embodiment, the pre-selected wavelength will be selected within +/−30 nm of the maximum peak emission. In yet another embodiment, the pre-selected wavelength will be selected within +/−50 nm of the maximum peak emission. In one exemplary embodiment, at least one of the pre-selected wavelengths will be in the range of about 300 to about 400 nm.

In one embodiment, the ratio of the fluorescence intensities will change during the authentication process by more than or equal to +/−5% as compared to the original or initial fluorescence ratio. That is, the ratio of fluorescence intensities can exhibit an increase or decrease of 5% as compared to the original or initial value. In another embodiment, the change will be greater than or equal to about +/−25%. In yet another embodiment, the change will be greater than or equal to about +/−95%. In yet another embodiment, the change in fluorescence ratio will be between about 5% and about 200%.

In addition, the authenticating signal of the authenticatable polymers containing the optically variable tags may also be the changing intensity of the fluorescence emission of the optically variable tag.

The changes in fluorescence emission can be detected by observing changes in the complete emission spectrum or changes in local parts of the spectrum (i.e. by looking at the discrete intensity of the fluorescence emission at the peak location of the tag emission) over time.

In one exemplary embodiment the change in intensity will be evaluated over time as a function of the difference between intensity at a time T1 and a time T2, T2 being greater than T1. In embodiment, there will be a difference of at least 10% between the signals at T1 and T2. In one embodiment where the authenticating signal is repeatable, the difference between the signals at T1 and T2 will be from 10 to 90%, while in another embodiment, the difference will be from 15 to 75%. In one exemplary embodiment, a repeatable authenticating signal will have a difference of from 20 to 40%. In another embodiment where the authenticating signal is not repeatable, the difference between the signals at T1 and T2 will be from 10 to 100%.

Suitable optically variable tags for use in the disclosed methods will generally be fluorescent or luminescent materials that are selected to be chemically compatible with the polymer matrix and have a heat stability consistent with engineering plastics compounding and in particular with the processing conditions of the polymer substrate. In one embodiment, the optically variable tags will be selected for their relatively good heat stability and compatibility with polycarbonate.

In one embodiment, the stable optically variable tags will be at least one of oxadiazole derivatives or luminescent conjugated polymers. Illustrative examples of suitable luminescent conjugated polymers are blue emitting luminescent polymers, such as poly-paraphenylenevinylene derivatives. Illustrative examples of suitable oxadiazole derivatives include oxadiazole derivatives substituted with a biphenyl or substituted byphenyl in the 2-position and with a phenyl derivative in the 5-position.

In one exemplary embodiment, the optically variable tag will be one of tert-butyl phenyl oxadiazole, bis(Biphenylyl) oxadiazole, or a mixture of tert-butyl phenyl oxadiazole and bis(Biphenylyl) oxadiazole. In one exemplary embodiment, the optically variable tag will be tert-butyl phenyl oxadiazole. In another exemplary embodiment, the optically variable tag will bis(Biphenylyl) oxadiazole.

The optically variable tag is added to the substrate polymer in an amount sufficient to be detected by fluorescence spectroscopy. In one embodiment, the optically variable tag will be present in the authenticatable polymer in an amount of no more than or equal to about 2% by weight, based on the weight of the authenticatable polymer. In another embodiment, the optically variable tag will be present in the authenticatable polymer in an amount of less than or equal to about $10^{-18}$% by weight, based on the total weight of the authenticatable polymer. In one exemplary embodiment, the optically variable tag will be present in the authenticatable polymer in an amount of less than or equal to about $10^{-12}$% by weight, based on the total weight of the authenticatable polymer. In yet another exemplary embodiment, the optically variable tag will be present in the authenticatable polymer in an amount of less than or equal to about $10^{-6}$% by weight, based on the total weight of the authenticatable polymer. In one embodiment, the optically variable tag will be present in the authenticatable polymer in an amount of at least 0.0001% by weight, based on the total weight of the authenticatable polymer. In another embodiment, the optically variable tag will be present in an authenticatable polymer or article, such as an optical storage disk, at a loading between 0.0001% and 0.05% by weight, based on the weight of the authenticatable polymer.

Non-optically variable compounds may optionally be used in the authenticatable polymers disclosed herein. In one exemplary embodiment, the non-optically variable compounds are fluorescent tags that are selected to enhance the signal from optically variable tags. Fluorescent tags as used herein refers to at least one of an organic fluorophore, an inorganic fluorophore, an organometallic fluorophore, a semiconducting luminescent nanoparticle, or combinations thereof. In addition, the fluorescent tags used are insensitive to polymer additives and to chemical and physical aging of the polymer.

In one exemplary embodiment, the fluorescent tags are selected from classes of dyes that exhibit high robustness against ambient environmental conditions and temperature stability of at least about 350° C., preferably at least about 375° C., and more preferably at least about 400° C. Typically, the fluorescent tags have temperature stability for a time period greater than or equal to about 20 seconds. In one embodiment, the fluorescent tags will have temperature stability for a time period greater than or equal to about 1 minute, while in another embodiment, the fluorescent tags will have temperature stability of greater than or equal to about 5 minutes. In one embodiment, the fluorescent tags will have temperature stability for a time period greater than or equal to about 10 minutes.

It is desirable to have optically variable tags and/or fluorescent tags hidden behind the matrix absorption. The matrix is defined herein as the backbone absorption from the polymer substrate or from any additive or colorant present in the tagged polymer formulation. In general, the enhancing fluorescent tags will be selected such that they have an excitation wavelength that overlaps with the absorption of the optically variable tags. In one embodiment, the fluorescent tags' emission and excitation wavelengths overlap with the ones of the optically variable tags. When such fluorescent tags are used, the detection wavelength at which the test signal is evaluated will typically be the maximum emission of the fluorescent tag and the authentication wavelength or wavelength spectrum will be the maximum excitation wavelength of the fluorescent tag. In one embodiment, the authentication wavelength or wavelength spectrum will be within +/−50 nm of the maximum excitation wavelength of the fluorescent tag, while in another embodiment, the authentication wavelength or wavelength spectrum will be within +/−30 nm of the maximum excitation wavelength of the fluorescent tag. In one exemplary embodiment, the authentication wavelength or wavelength spectrum will be within +/−10 nm of the maximum excitation wavelength of the fluorescent tag.

The excitation range of suitable fluorescent tags is typically about 100 nanometers to about 1100 nanometers, and more typically about 200 nanometers to about 1000 nanometers, and most typically about 250 nanometers to about 950 nanometers. The emission range of suitable fluorescent tags is typically about 250 nanometers to about 2500 nanometers.

Illustrative fluorescent tags include fluorescent tags such as the following but are not limited to, dyes such as polyazaindacenes or coumarins, including those set forth in U.S. Pat. No. 5,573,909. Other suitable families of dyes include lanthanide complexes, hydrocarbon and substituted hydrocarbon dyes; polycyclic aromatic hydrocarbons; scintillation dyes (preferably oxazoles and oxadiazoles); aryl- and heteroaryl-substituted polyolefins (C2–C8 olefin portion); carbocyanine dyes; phthalocyanine dyes and pigments; oxazine dyes; carbostyryl dyes; porphyrin dyes; acridine dyes; anthraquinone dyes; anthrapyridone dyes; naphtalimide dyes; benzimidazole derivatives; arylmethane dyes; azo dyes; diazonium dyes; nitro dyes; quinone imine dyes; tetrazolium dyes; thiazole dyes; perylene dyes, perinone dyes, bis-benzoxazolylthiophene (BBOT), xanthene and thioxanthene dyes, and indigoid and thioindigoid dyes. Fluorescent tags also include anti-stokes shift dyes that absorb in the near infrared wavelength and emit in the visible wavelength.

The following is a partial list of commercially available, suitable fluorescent and/or luminescent dyes useful as the fluorescent tag: 5-Amino-9-diethyliminobenzo(a)phenoxazonium Perchlorate7-Amino-4-methylcarbostyryl, 7-Amino-4-methylcoumarin, 7-Amino-4-trifluoromethylcoumarin, 3-(2'-Benzimidazolyl)-7-N,N-diethylaminocoumarin, 3-(2'-Benzothiazolyl)-7-diethylaminocoumarin, 2-(4-Biphenylyl)-5-(4-t-butylphenyl)-1,3,4-oxadiazole, 2-(4-Biphenylyl)-5-phenyl-1,3,4-oxadiazole, 2-(4-Biphenyl)-6-phenylbenzoxazole-1,3, 2,5-Bis-(4-biphenylyl)-1,3,4-oxadiazole, 2,5-Bis-(4-biphenylyl)-oxazole, 4,4'-Bis-(2-butyloctyloxy)-p-quaterphenyl, p-Bis(o-methylstyryl)-benzene, 5,9-Diaminobenzo(a)phenoxazonium Perchlorate, 4-Dicyanomethylene-2-methyl-6-(p-dimethylaminostyryl)-4H-pyran, 1,1'-Diethyl-2,2'-carbocyanine Iodide, 1,1'-Diethyl-4,4'-carbocyanine Iodide, 3,3'-Diethyl-4,4',5,5'-dibenzothiatricarbocyanine Iodide, 1,1'-Diethyl-4,4'-dicarbocyanine Iodide, 1,1'-Diethyl-2,2'-dicarbocyanine Iodide, 3,3'-Diethyl-9,11-neopentylenethiatricarbocyanine Iodide, 1,3'-Diethyl-4,2'-quinolyloxacarbocyanine Iodide, 1,3'-Diethyl-4,2'-quinolylthiacarbocyanine Iodide, 3-Diethylamino-7-diethyliminophenoxazonium Perchlorate, 7-Diethylamino-4-methylcoumarin, 7-Diethylamino-4-trifluoromethylcoumarin, 7-Diethylaminocoumarin, 3,3'-Diethyloxadicarbocyanine Iodide, 3,3'-Diethylthiacarbocyanine Iodide, 3,3'-Diethylthiadicarbocyanine Iodide, 3,3'-Diethylthiatricarbocyanine Iodide, 4,6-Dimethyl-7-ethylaminocoumarin, 2,2'-Dimethyl-p-quaterphenyl, 2,2-Dimethyl-p-terphenyl, 7-Dimethylamino-1-methyl-4-methoxy-8-azaquinolone-2,7-Dimethylamino-4-methylquinolone-2,7-Dimethylamino-4-trifluoromethyl coumarin, 2-(4-(4-Dimethylaminophenyl)-1,3-butadienyl)-3-ethylbenzothiazolium Perchlorate, 2-(6-(p-Dimethylaminophenyl)-2,4-neopentylene-1,3,5-hexatrienyl)-3-methylbenzothiazolium Perchlorate, 2-(4-(p-Dimethylaminophenyl)-1,3-butadienyl)-1,3,3-trimethyl-3H-indolium Perchlorate, 3,3'-Dimethyloxatricarbocyanine Iodide, 2,5-Diphenylfuran, 2,5-Diphenyloxazole, 4,4'-Diphenylstilbene, 1-Ethyl-4-(4-(p-Dimethylaminophenyl)-1,3-butadienyl)-pyridinium Perchlorate, 1-Ethyl-2-(4-(p-Dimethylaminophenyl)-1,3-butadienyl)-pyridinium Perchlorate, 1-Ethyl-4-(4-(p-Dimethylaminophenyl)-1,3-butadienyl)-quinolium Perchlorate, 3-Ethylamino-7-ethylimino-2,8-dimethylphenoxazin-5-ium Perchlorate, 9-Ethylamino-5-ethylamino-10-methyl-5H-benzo(a)phenoxazonium Perchlorate, 7-Ethylamino-6-methyl-4-trifluoromethylcoumarin, 7-Ethylamino-4-trifluoromethylcoumarin, 1,1',3,3,3',3'-Hexamethyl-4,4',5,5'-dibenzo-2,2'-indotricarboccyanine Iodide, 1,1',3,3,3',3'-Hexamethylindodicarbocyanine Iodide, 1,1',3,3,3',3'-Hexamethylindotricarbocyanine Iodide, 2-Methyl-5-t-butyl-p-quaterphenyl, N-Methyl-4-trifluoromethylpiperidino-<3,2-g>coumarin, 3-(2'-N-Methylbenzimidazolyl)-7-N,N-diethylaminocoumarin, 2-(1-Naphthyl)-5-phenyloxazole, 2,2'-p-Phenylen-bis(5-phenyloxazole), 3,5,3"",5""-Tetra-t-butyl-p-sexiphenyl, 3,5,3"",5""-Tetra-t-butyl-p-quinquephenyl, 2,3,5,6-1H,4H-Tetrahydro-9-acetylquinolizino-<9,9a,1-gh>coumarin, 2,3,5,6-1H,4H-Tetrahydro-9-carboethoxyquinolizino-<9,9a,1-gh>coumarin, 2,3,5,6-1H,4H-Tetrahydro-8-methylquinolizino-<9,9a,1-gh>coumarin, 2,3,5,6-1H,4H-Tetrahydro-9-(3-pyridyl)-quinolizino-<9,9a,1-gh>coumarin, 2,3,5,6-1H,4H-Tetrahydro-8-trifluoromethylquinolizino-<9,9a,1-gh>coumarin, 2,3,5,6-1H,4H-Tetrahydroquinolizino-<9,9a,1-gh>coumarin, 3,3,',2",3"'-Tetramethyl-p-quaterphenyl, 2,5,2"",5"'-Tetramethyl-p-quinquephenyl, P-terphenyl, P-quaterphenyl, Nile Red, Rhodamine 700, Oxazine 750, Rhodamine 800, IR 125, IR 144, IR 140, IR 132, IR 26, IR5, Diphenylhexatriene, Diphenylbutadiene, Tetraphenylbutadiene, Naphthalene, Anthracene, 9,10-diphenylanthracene, Pyrene, Chrysene, Rubrene, Coronene, Phenanthrene.

Fluorescent tags as used herein also include luminescent nanoparticles of sizes from about 1 nanometer to about 50 nanometers. Exemplary luminescent nanoparticles include, but are not limited to, semi-conducting nanoparticles like CdS, ZnS, Cd3 P2, PbS, or combinations thereof. Other luminescent nanoparticles also include rare earth aluminates including, but not limited to, strontium aluminates doped with Europium and Dysprosium.

In one embodiment, fluorescent tags such as perylenes such as Anthra[2,1,9-def:6,5,10-d'e'f']diisoquinoline-1,3,8,10(2H,9H)-tetrone, 2,9-bis[2,6-bis (1-methylethyl)phenyl]-5,6,12,13-tetraphenoxy are utilized as the fluorescent tags.

The concentration of the fluorescent tags depends on the quantum efficiency of the tag, excitation and emission wavelengths, and employed detection techniques, and will generally be present in an amount of about $10^{-19}$ percent by weight to about 2 percent by weight of the authentication polymer. In another embodiment the fluorescent tag will be present in an amount of about $10^{-15}$ percent by weight to about 0.5 percent by weight of the authentication polymer. In one exemplary embodiment, the fluorescent tag will be present in an amount of about $10^{-12}$ percent by weight to about 0.05 percent by weight of the authentication polymer.

The determination of a test signal of the test polymer will generally be done with the foreknowledge of the particular fluorescence emission of the authenticatable polymer for which a confirmation is desired. The particular fluorescence emission of an authenticatable polymer will depend upon a variety of factors such as the nature of the optically variable tag, the loading of the optically variable tag, the presence of a fluorescent tag, the loading of a fluorescent tag, the nature of a fluorescent tag, the type of substrate polymer and the like. The unavailability of such foreknowledge is an advantage of the disclosed method.

The test polymer to be authenticated will be exposed to a stimulus capable of exciting the optically variable tag to fluoresce or emit. Examples of suitable stimulus include electromagnetic radiation (i.e. light) sources such as lamps, lasers, light emitting diodes (LEDS), and the like.

In one embodiment, the test polymer will be exposed to a electromagnetic radiation of about 160 to 1100 nm, while in another embodiment, the test polymer will be exposed to a electromagnetic radiation of about 250 to 750 nm. In one exemplary embodiment, the test polymer will be exposed to an electromagnetic radiation of about 300 to 700 nm.

The test polymer will be exposed to the stimulus for a period sufficient to obtain the test signal. In one embodiment, the period of exposure will be no less than or equal to 1 second, while in another embodiment, the period of exposure will be no more than or equal to about 10 minutes. In one embodiment, the period of exposure will be about 1 to 600 seconds, while in another; the period of exposure will be about 5 to 300 seconds. Note that the period of exposure to the stimulus depends on the intensity of the stimulus and the sensitivity of the chemistry. For faster response time (i.e. shorter stimulus periods), laser light sources are preferred.

In one embodiment, the fluorescence emission of the optically variable tag will exhibit a first wavelength and then a second wavelength during authentication.

In one embodiment, the fluorescence emission of the optically variable tag will vary over a wavelength range of about 2 to about 300 nm from its initial position. In another embodiment, the fluorescence emission will vary from 5 to 200 nm. In yet another embodiment, the fluorescence emission will vary from 10 to 100 nm.

The test signal may be any of the signals used as the authentication signal discussed above in regards to the optically variable tag and the authenticatable polymer. That is, the test signal may be a determination of the variable peak location or shifting wavelength, the difference in intensity at T1 and T2, the variable ratio of fluorescence intensities at two or more pre-selected wavelengths and combinations of these signals as well as calculations based on any of these signals.

Test signals may be determined using analytical techniques such as fluorescence spectroscopy and luminescence spectroscopy. In one exemplary embodiment, the test signal will be determined using fluorescence spectroscopy.

In another embodiment, the detection of the changes in fluorescence emission from exposure to a stimulus that causes fluorescence will be done at the thinner edge of the article (edge fluorescence) while the light source used for the excitation illuminates the article from the top.

A test polymer may be authenticated as an authenticatable polymer if the test signal is substantially the same as an authenticating signal of the authenticatable polymer. In one embodiment, this will mean that the test signals for both the test polymer and the authenticatable polymer will have a difference in value of less than or equal to about 5%. In other embodiments, variations between the test signals of the test polymer and the authenticatable polymer of up to +/−20% can be tolerated for substantially similar signals, while in other embodiments, variations of less than about +/−10% will be found for substantially similar signals.

In addition to the substrate polymer, the optically variable tag, and fluorescent tags, the authenticatable polymers disclosed herein may optionally include various additives ordinarily incorporated in resin compositions of this type. Such additives may include antioxidants, heat stabilizers, antistatic agents (tetra alkylammonium benzene sulfonate salts, tetra alkylphosphonium benzene sulfonate salts, and the like), mold releasing agents (pentaerythritol tetrastearate; glycerol monstearate, and the like), and the like, and combinations comprising the foregoing. For example, the authenticatable polymer composition can comprise heat stabilizer from about 0.01 weight percent to about 0.1 weight percent; an antistatic agent from about 0.01 weight percent to about 1 weight percent; and a mold releasing agent from about 0.1 weight percent to about 1 weight percent of a mold releasing agent; based upon the total weight of the authenticatable polymer.

Some possible antioxidants include, for example, organophosphites, e.g., tris(nonyl-phenyl)phosphite, tris(2,4-di-t-butylphenyl)phosphite, bis(2,4-di-t-butylphenyl)pentaerythritol diphosphite, distearyl pentaerythritol diphosphite and the like; alkylated monophenols, polyphenols and alkylated reaction products of polyphenols with dienes, such as, for example, tetrakis[methylene(3,5-di-tert-butyl-4-hydroxyhydrocinnamate)]methane, 3,5-di-tert-butyl-4-hydroxyhydrocinnamate octadecyl, 2,4-di-tert-butylphenyl phosphite, and the like; butylated reaction products of para-cresol and dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds, such as, for example, distearylthiopropionate, dilaurylthiopropionate, ditridecylthiodipropionate, and the like; amides of beta-(3,5-di-tert-butyl-4-hydroxyphenyl)-propionic acid; and the like, as well as combinations comprising a of the foregoing.

Other potential additives which may be employed comprise: UV absorbers; stabilizers such as light and thermal stabilizers (e.g., acidic phosphorous-based compounds); hindered phenols; zinc oxide, zinc sulfide particles, or combination thereof; lubricants (mineral oil, and the like), plasticizers, dyes used as a coloring material (quinines, azobenzenes, and the like); among others, as well as combinations comprising a of the foregoing additives.

In order to aid in the processing of the authenticatable polymer, particularly when the polymer is polycarbonate, catalyst(s) may also be employed, namely in the extruder or other mixing device. The catalyst typically assists in controlling the viscosity of the resulting material. Possible catalysts include hydroxides, such as tetraalkylammonium hydroxide, tetraalkylphosphonium hydroxide, and the like, with diethyldimethylammonium hydroxide and tetrabutylphosphonium hydroxide preferred. The catalyst(s) can be employed alone or in combination with quenchers such as acids, such as phosphoric acid, and the like. Additionally, water may be injected into the polymer melt during compounding and removed as water vapor through a vent to remove residual volatile compounds.

The authenticatable polymers disclosed herein are produced by using a reaction vessel capable of adequately mixing various precursors, such as a single or twin screw extruder, kneader, blender, or the like.

Methods for incorporating the optically variable tag and optionally the fluorescent tags, into the substrate polymer include, for example, coating, admixing, blending, or copolymerization. The optically variable tags can be incorporated into the substrate polymer such that they are uniformly dispersed throughout the authenticatable polymer or such that they are dispersed on a portion of the authenticatable polymer. In one exemplary embodiment, the optically variable tags will be incorporated into the substrate polymer such that they are uniformly dispersed throughout the authenticatable polymer. The optically variable tags and the fluorescent tags can be incorporated into the substrate polymer in the polymer manufacturing stage, during the polymer compounding step, during polymer processing into articles, or combinations thereof. It is possible to incorporate both the optically variable tags and the fluorescent tags simultaneously or separately. In one embodiment, the optically variable tags and optional fluorescent tags will be introduced using a concentrate (i.e. masterbatch) either during the polymer compounding stage or during the article forming.

For example, the polymer precursors for the substrate polymer can be premixed with the optically variable tags and the fluorescent tags (e.g., in a pellet, powder, and/or liquid form) and simultaneously fed through a hopper into the extruder, or the optically variable tags and the fluorescent tags can be optionally added in the feed throat or through an alternate injection port of the injection molding machine or other molding. Optionally, in one embodiment, a substrate polymer can be produced and the optically variable tags and the fluorescent tags can be dispersed on a portion of a substrate polymer by coating, molding, or welding on a portion of an authenticatable polymer there to. In one exemplary embodiment, the optically variable tags and optional fluorescent tags will be homogenously distributed unless they were placed in a carrier that is not miscible with the substrate polymer.

In one embodiment, the optically variable tags will be incorporated into the substrate polymer by admixing, blending, compounding or copolymerization. In one exemplary embodiment, the optically variable tags will be incorporated into the polymer by forming a dry blend of the optically variable tags in the substrate polymer and compounding the resulting mixture.

In one embodiment, the fluorescent tags will be incorporated into the substrate polymer by admixing, blending, compounding or copolymerization. In one exemplary embodiment, the fluorescent tags will be incorporated into the substrate polymer by adding the fluorescent tags in the melt during the compounding step. Such additions may, in one embodiment, be done via a side feeder.

In another embodiment, the optically variable tags and the fluorescent tags will be incorporated into the substrate polymer by adding the optically variable tags and fluorescent tags in the melt during the compounding. In one embodiment, such additions may be done via a side feeder. In another exemplary embodiment, the optically variable tags and the fluorescent tags will be incorporated by compounding using a twin-screw extruder and adding the optically variable tags and fluorescent tags to the melt via a side feeder.

When the substrate polymer precursors are employed, the extruder should be maintained at a sufficiently high temperature to melt the polymer precursors without causing decomposition thereof. For polycarbonate, for example, temperatures of about 220° C. to about 360° C. can be used in one embodiment. In another embodiment temperatures of about 260° C. to about 320° C. are utilized. Similarly, the residence time in the extruder should be controlled to minimize decomposition. Residence times of up to about 2 minutes or more can be employed, with up to about 1.5 minutes used in one embodiment, and up to about 1 minute used in another exemplary embodiment. Prior to extrusion into the desired form (typically pellets, sheet, web, or the like, the resulting mixture can optionally be filtered, such as by melt filtering and/or the use of a screen pack, or the like, to remove undesirable contaminants or decomposition products.

The authenticatable polymers may be used for any application in which the physical and chemical properties of the material are desired. In one embodiment, the authenticatable polymers are used to make formed articles such as data storage media. In one exemplary embodiment, the authenticatable polymers will be used to make data storage media such as CDs and DVDs. Other embodiments include packaging material (and especially drug packaging), automotive parts like lenses, telecom accessories (like cell phone covers), computers and consumer electronics, construction materials, medical devices, eyewear products, films and sheets (including those used in display applications) and the like.

After the authenticatable polymer composition has been produced, it can be formed into a data storage media using various molding techniques, processing techniques, or combination thereof. Possible molding techniques include injection molding, film casting, extrusion, press molding, blow molding, stamping, and the like. One possible process comprises an injection molding-compression technique where a mold is filled with a molten polymer. The mold may contain a preform, inserts, fillers, etc. The authenticatable polymer is cooled and, while still in an at least partially molten state, compressed to imprint the desired surface features (e.g., pits, grooves, edge features, smoothness, and the like), arranged in spiral concentric or other orientation, onto the desired portion(s) of the formed part, i.e. one or both sides in the desired areas. The formed part is then cooled to room temperature. Once the formed part has been produced, additional processing, such as electroplating, coating techniques (spin coating, spray coating, vapor deposition, screen printing, painting, dipping, and the like), lamination, sputtering, and combinations comprising a of the foregoing processing techniques, among others known in the art, may be employed to dispose desired layers on the substrate.

An example of a polycarbonate data storage media comprises an injection molded polycarbonate substrate that may optionally comprise a hollow (bubbles, cavity, and the like) or filled (metal, plastics, glass, ceramic, and the like, in various forms such as fibers, spheres, particles, and the like) core.

In one embodiment when a formed authenticatable or test article is a data storage media, the authenticatable polymer will preferably be used to form the substrate(s) that will be read through by a laser in a data storage media player device. The reason is that it is significantly more difficult to fake the response of an authenticatable polymer and ensure that the technology used does not impact playability of the media In a data storage media having two substrates, such as a DVD, one or both substrates can be formed using the authenticatable polymers. In one exemplary embodiment, the substrate of a DVD formed of the authenticatable polymer will be the layer read by a laser in a DVD player device.

Disposed on the substrate are various layers including: a data layer, dielectric layer(s), a reflective layer(s), and/or a protective layer, as well as combinations comprising the foregoing layers. These layers comprise various materials and are disposed in accordance with the type of media produced.

For example, for a first surface media, the layers may be protective layer, dielectric layer, data storage layer, dielectric layer, and then the reflective layer disposed in contact with the substrate, with an optional decorative layer disposed on the opposite side of the substrate. Meanwhile, for an optical media, the layers may be optional decorative layer, protective layer, reflective layer, dielectric layer, and data storage layer, with a subsequent dielectric layer in contact with the substrate. Optical media may include, but is not limited to, any conventional pre-recorded, re-writable, or recordable formats such as: CD, CD-R, CD-RW, DVD, DVD-R, DVD-RW, DVD+RW, DVD-RAM, high-density DVD, magneto-optical, and others. It is understood that the form of the media is not limited to disk-shape, but may be any shape which can be accommodated in a readout device.

The data storage layer(s) may comprise any material capable of storing retrievable data, such as an optical layer, magnetic layer, or a magneto-optic layer. Typically the data layer has a thickness of up to about 600 Angstroms (Å) or so, with a thickness up to about 300 Å preferred. Possible data storage layers include, but are not limited to, oxides (such as silicone oxide), rare earth elements—transition metal alloys, nickel, cobalt, chromium, tantalum, platinum, terbium, gadolinium, iron, boron, others, and alloys and combinations comprising a of the foregoing, organic dye (e.g., cyanine or phthalocyanine type dyes), and inorganic phase change compounds (e.g., TeSeSn, InAgSb, and the like).

The protective layer(s), which protect against dust, oils, and other contaminants, can have a thickness of greater than about 100 microns (μ) to less than about 10 Å in one embodiment, with a thickness of about 300 Å or less in other embodiments, and a thickness of about 100 Å or less in other exemplary embodiments. The thickness of the protective layer(s) is usually determined, at least in part, by the type of read/write mechanism employed, e.g., magnetic, optic, or magneto-optic. Possible protective layers include anti-corrosive materials such as gold, silver, nitrides (e.g., silicon nitrides and aluminum nitrides, among others), carbides (e.g., silicon carbide and others), oxides (e.g., silicon dioxide and others), polymeric materials (e.g., polyacrylates or polycarbonates), carbon film (diamond, diamond-like carbon, and the like), among others, and combinations comprising a of the foregoing.

The dielectric layer(s), which are disposed on one or both sides of the data storage layer and are often employed as heat controllers, can typically have a thickness of up to or exceeding about 1,000 Å and as low as about 200 Å or less. Possible dielectric layers include nitrides (e.g., silicon nitride, aluminum nitride, and others); oxides (e.g., aluminum oxide); carbides (e.g., silicon carbide); and combinations comprising of the foregoing materials, among other materials compatible within the environment and preferably not reactive with the surrounding layers.

The reflective layer(s) should have a sufficient thickness to reflect a sufficient amount of energy (e.g., light) to enable data retrieval. Typically the reflective layer(s) can have a thickness of up to about 700 Å or so, with a thickness of about 300 Å to about 600 Å being used in some exemplary embodiments. Possible reflective layers include any material capable of reflecting the particular energy field, including metals (e.g., aluminum, silver, gold, titanium, silicon, and alloys and mixtures comprising a of the foregoing metals, and others).

In addition to the data storage layer(s), dielectric layer(s), protective layer(s) and reflective layer(s), other layers can be employed such as lubrication layer and others. Useful lubricants include fluoro compounds, especially fluoro oils and greases, and the like.

In one embodiment, the authenticatable polymers will be formed into the substrate of a data storage media. In one exemplary embodiment, the authenticatable polymer will comprise the substrate of an optical storage media. In one particularly exemplary embodiment, the authenticatable polymer will comprise at least one substrate of a digital versatile disk (DVD).

Illustrative DVDs comprising the authenticatable polymers disclosed herein comprise two bonded plastic substrates (or resin layers), each typically having a thickness less than or equal to about 1.0 millimeter (mm), with a thickness of less than or equal to about 0.7 mm preferred. A thickness of greater than or equal to about 0.4 mm is also preferred. At least one of the two bonded plastic substrates comprises one or more layers of data. The first layer, generally called layer zero (or L0), is closest to the side of the disk from which the data is read (readout surface). The second layer, generally called layer 1 (L1), is further from the readout surface. Disposed between L0 (3) and L1 (5) are typically an adhesive and optionally a protective coating or separating layer. Single sided DVD's (i.e., those that will be read from a single readout surface disposed on one side of the DVD), can additionally comprise a label disposed on the side of the DVD opposite the readout surface. In one embodiment, one or both of the first layer and the second layer will be comprised of the authenticatable polymers. In one exemplary embodiment, the first layer will be comprised of the authenticatable polymer.

In the case of a single layer read from a readout surface (e.g. DVD 5, DVD 10), a stamped surface is covered with a thin reflective data layer by a sputtering or other deposition process. This creates a metallic coating typically about 60 to about 100 angstroms (Å) thick. For two data layer DVDs that are read from the same readout surface (e.g. DVD 9, DVD 14, DVD 18), the laser must be able to reflect from the first layer when reading it, but also focus (or transmit) through the first layer when reading the second layer. Therefore, the first layer is "semi-transparent" (i.e., semi-reflective), while the second layer is "fully-reflective". Under current standards set by the Consortium for Optical Media, metallization combination for the fully-reflective and semi-reflective data layers, as measured per the electrical parameter R14H (as described in ECMA specifications #267), should be about 18 percent (%) to about 30% at the wavelength of the laser. In the present DVD's, the laser wavelength generally employed is less than or equal to about 700 nm, with about 400 nm to about 675 nm preferred, and about 600 nm to about 675 nm more preferred. Although these metallization standards were set for DVD data layers employed with colorless, optical quality resin, they are equally applied to DVD systems with colored resin.

When color is added to the resin, light transmission through and reflected from the substrate is effected. The metallization nature and thickness on the semi-reflective and fully reflective (L0 and L1) layers is adapted for the light transmission of the substrate. Desired reflectivity can be obtained by balancing the metallization thickness with the reflectivity of the semi-reflective data layer, and by adjusting the thickness of the fully reflective data layer to ensure its reflectivity is within the desired specification.

Metallization for the individual data layer(s) can be obtained using various reflective materials. Materials, e.g., metals, alloys, and the like, having sufficient reflectivity to be employed as the semi-reflective and/or fully reflective data layers, and which can preferably be sputtered onto the substrate, can be employed. Some possible reflective materials comprise gold, silver, platinum, silicon, aluminum, and the like, as well as alloys and combinations comprising at least one of the foregoing materials. For example, the first/second reflective data layer metallization can be gold/aluminum, silver alloy/aluminum, silver alloy/silver alloy, or the like.

In addition to the overall reflectivity of each layer, the difference in reflectivity between subsequent reflective data layers should be controlled, in order to ensure sufficient reflectivity of the subsequent layer. Preferably, the difference in reflectivity between subsequent layers (e.g., the first and second layers) is less than or equal to about 5%, with less than or equal to about 4% preferred, and less than or equal to about 3.0% more preferred. It is further preferred to have a reflectivity difference between the adjacent reflective data layers of greater than or equal to about 0.5%, with greater than or equal to about 1% more preferred. It should be noted that although described in relation to two layers, it is understood that more than two layers could be employed, and that the difference in reflectivity between subsequent layers should be as set forth above.

The reflective data layers are typically sputtered or otherwise disposed on a pattern (e.g., surface features such as pits, grooves, asperities, start/stop orientator, and/or the like) formed into a surface of the substrate via molding, embossing, or the like. Depositions, for example, can comprise sputtering a semi-reflective data layer over a first patterned surface. A separator layer or protective coating can then be disposed over the semi-reflective data layer. If a multiple data layer DVD (e.g., DVD 14, DVD 18, or the like) is to be formed, a $2^{nd}$ patterned surface can be formed (e.g., stamped or the like) in the side of the separator layer opposite the semi-reflective data layer. A fully reflective data layer can then be sputtered or otherwise deposited on the separator layer. Alternatively, for DVD 14 construction, the fully reflective data layer can be deposited on a patterned surface of a $2^{nd}$ substrate (or resin layer). A separate layer or protective coating is then disposed on one or both of the semi-reflective data layer and the fully reflective data layer. A bonding agent or adhesive can then be disposed between the two substrates and they can be bonded together to form a disk. Optionally, several semi-reflective data layers can be deposited with a separator layer between each subsequent layer.

The reflectivity of the reflective data layer(s) can be about 5% to about 100%, depending upon the number of reflective layers. If a single reflective data layer is employed, the reflectivity is preferably about 30% to about 100%, with about 35% to about 90% more preferred, and about 45% to about 85% even more preferred. If a dual reflective data layer is employed, the reflectivity of the data layers is preferably about 5% to about 45%, with about 10% to about 40% more preferred, about 15% to about 35% even more preferred, and about 18% to about 30% especially preferred. Finally, if multiple reflective data layers (e.g., greater than 2 reflective data layers readable from a single reading surface) are employed, the reflectivity is preferably about 5% to about 30%, with about 5% to about 25% more preferred. The especially preferred ranges are currently based upon the ECMA specification #267, wherein the reflectivity is either about 18% to about 30% reflectivity for a dual layered DVD (e.g., at least one fully reflective layer and at least one semi-reflective layer) or about 45% to about 85% reflectivity for a single layer DVD (e.g., one fully reflective layer).

In one embodiment, the authenticatable polymers used to make these DVD substrates will enables the transmission of about 60% to less than 94% of light therethrough, in the wavelength region of the laser. Within that transmission range, preferably, the transmissivity is greater than or equal to about 70%, with greater than or equal to about 74% more preferred, and greater than or equal to about 78% especially preferred. Depending upon the type and amount of colorant employed, the transmissivity can be less than or equal to about 92%, with less than or equal to about 88% and even less than or equal to about 85% possible, depending upon the type of colorant. It should be noted that as the transmissivity of the substrate decreases, the ability to attain the desired adhesion of the substrates becomes more difficult. Preferably, the substrate comprises polycarbonate, with a primarily polycarbonate (e.g., greater than or equal to about 80% polycarbonate) substrate especially preferred.

EXAMPLES

Example 1

Preparation of Samples According to the Invention

Optically variable organic fluorophores were used as spectroscopic tags. The type and concentrations of the tags are presented in Table 1. The tags were incorporated into the substrate polycarbonate material during the molding process. Fluorescence emission spectra of the tags were measured continuously over about 2.5 min to assess the spectral signatures of the tags and the changes of these spectral signatures. Determinations were performed on a setup that included a miniature laser light source (Nanolase, France, 355 nm emission wavelength) and a portable spectrofluorometer (Ocean Optics, Inc., Dunedin, Fla., Model ST2000). The spectrofluorometer was equipped with a 200-μm slit, 600-grooves/mm grating blazed at 400 nm and covering the spectral range from 250 to 800 nm with efficiency greater than 30%, and a linear CCD-array detector. Light from the laser was focused into one of the arms of a "six-around-one" bifurcated fiber-optic reflection probe (Ocean Optics, Inc., Model R400-7-UV/VIS). Light from the samples was collected when the common end of the fiber-optic probe was positioned near the samples at a certain angle to minimize the amount of light directly reflected from the sample back into the probe. The second arm of the probe was coupled to the spectrofluorometer.

TABLE 1

Organic UV fluorophores used as spectroscopic tags.

| Tag Fluorophore | Loading of Tag | Code of Samples |
|---|---|---|
| tert-butyl phenyl oxadiazole | 0.01, 0.005 and 0.001 pph | MWB0312033-1, 2, 3 |
| bis(Biphenylyl) oxadiazole | 0.01, 0.005 and 0.001 pph | MWB0312034-1, 2, 3 |
| Control OQ1030 DVD substrate | 0 | |

Example 2

Experimental Results Using Tert-butyl phenyl Oxadiazole

FIG. 1 depicts time dependent fluorescence spectra of the fluorescent tag tert-butyl phenyl oxadiazole incorporated into polycarbonate and an OQ1030 DVD substrate used as a control. FIG. 1 illustrates two important aspects of the invention. Under a properly selected UV excitation, fluorescence of the polycarbonate and the tag exhibit time dependence. The fluorescence intensity decreases during a short measurement time (time scale=2–3 min or less). This time dependence originates from the interactions of the UV light with the polymer and the tag. This time dependent fluorescence serves as a new type of tag discrimination tool. FIG. 1 also illustrates the discrimination between a control and tag levels at 0.01, 0.005 and 0.001 pph at both the early and late stages of measurement. The simplest discrimination is by the determination of the fluorescence intensity as shown in FIG. 1.

Figure 2:
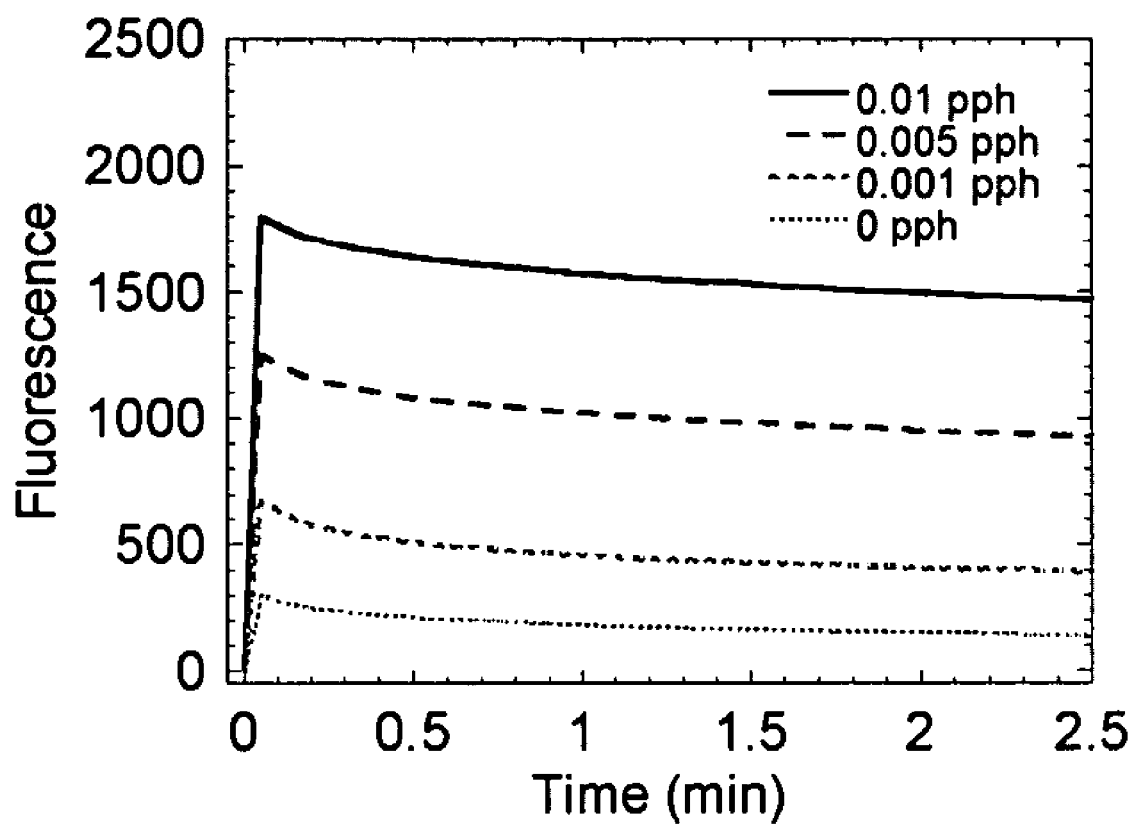
FIG. 2 is graphical representation of the time-dependent fluorescence intensity at 386 nm of samples with different levels of tert-butyl phenyl oxadiazole incorporated into polycarbonate.
Figure 3:
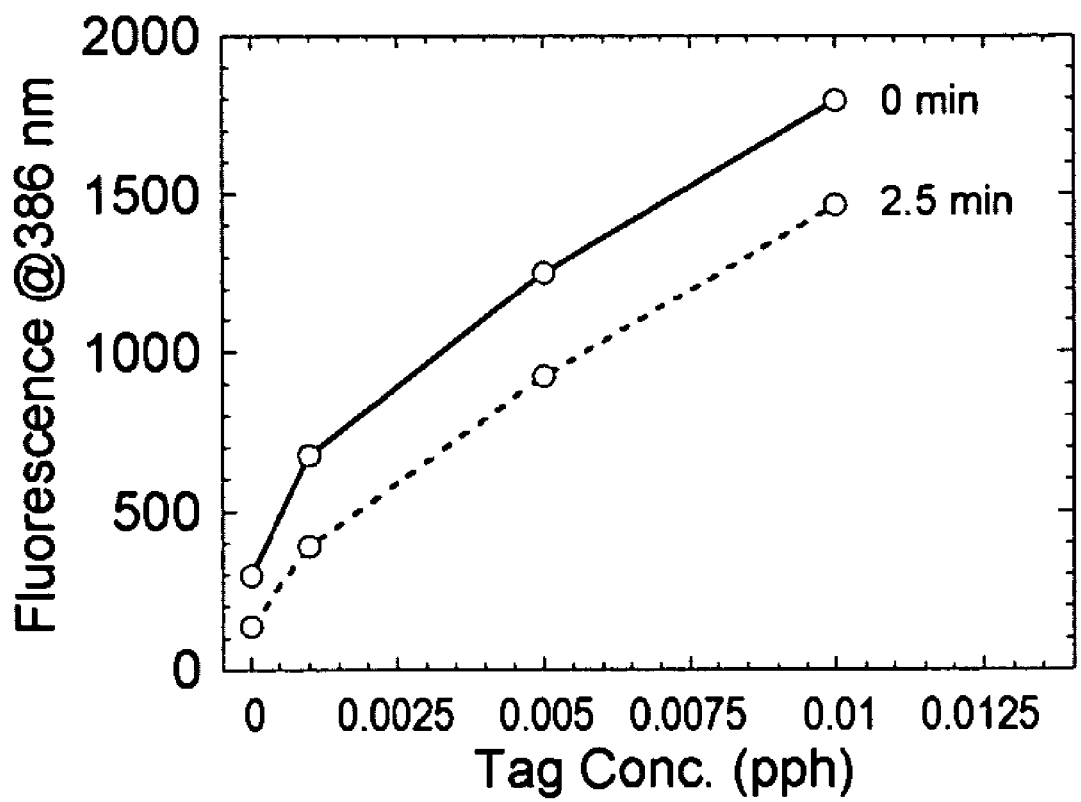
FIG. 3 is an illustration of the calibration curves of fluorescence intensity at 386 nm as a function of the concentration of tert-butyl phenyl oxadiazole in polycarbonate.

Fluorescence intensity decreases as a function of measurement time as shown in FIG. 2. This fluorescence decrease is observed for all samples, without and with the tag. Overall, the calibration plots that relate the fluorescence at 386 nm and the tag concentration are shown in FIG. 3 for the initial and final phases of the measurements (0 and 2.5 min after the start of the measurement).

Figure 4:
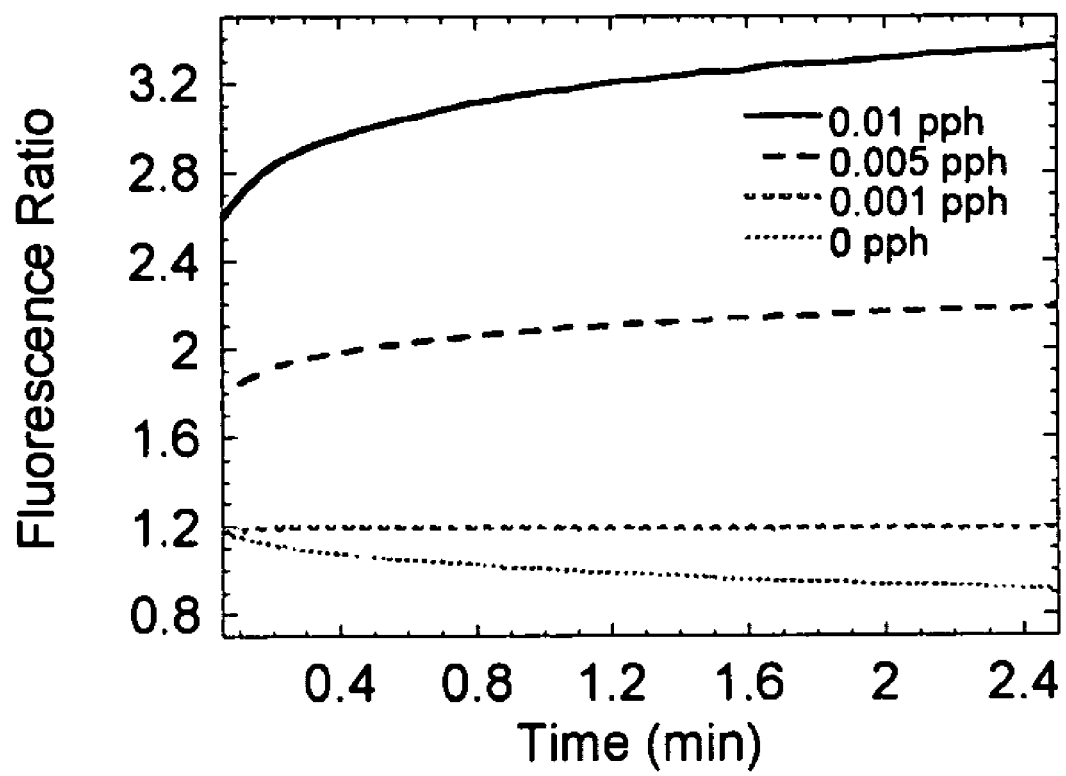
FIG. 4 is a graphical representation that illustrates that the ratio of fluorescence intensities of two properly selected fluorescence wavelengths decreases as a function of measurement time if the tag is absent in the substrate polymer and increases if the tag is present at different levels.
Figure 5:
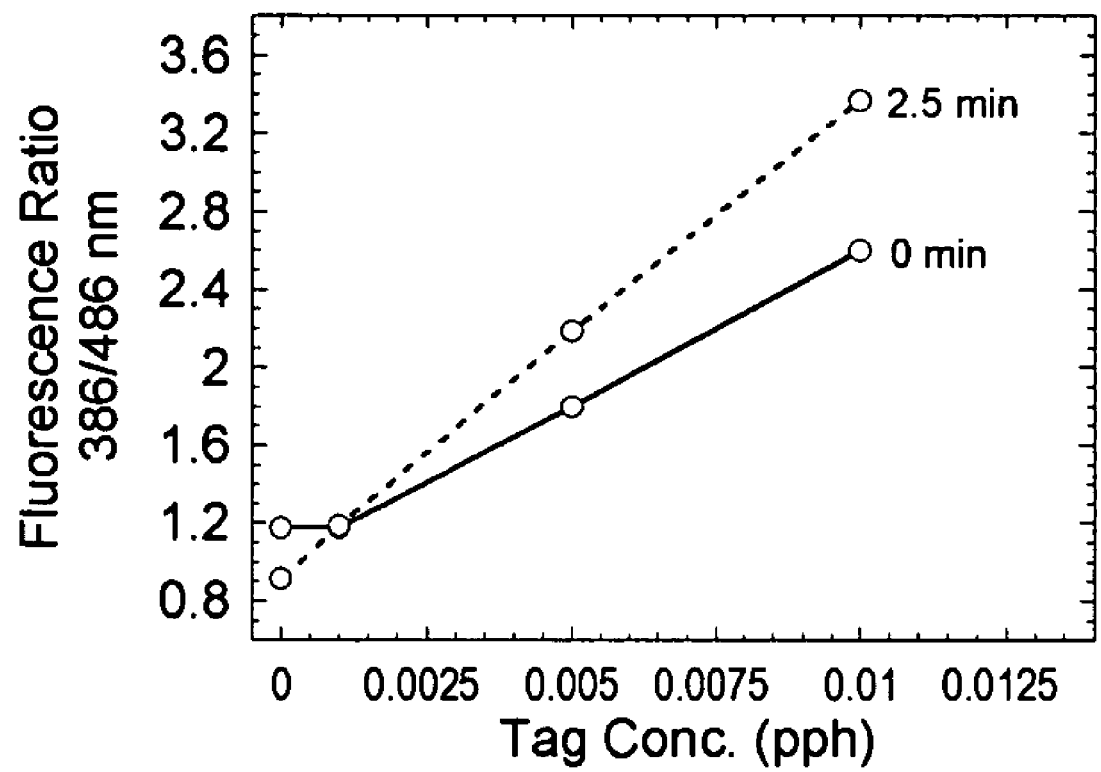
FIG. 5 is an illustration of the direct correlation between the level of the tag in the polymer and fluorescence ratio after 2.5 min of measurements.
Figure 6:
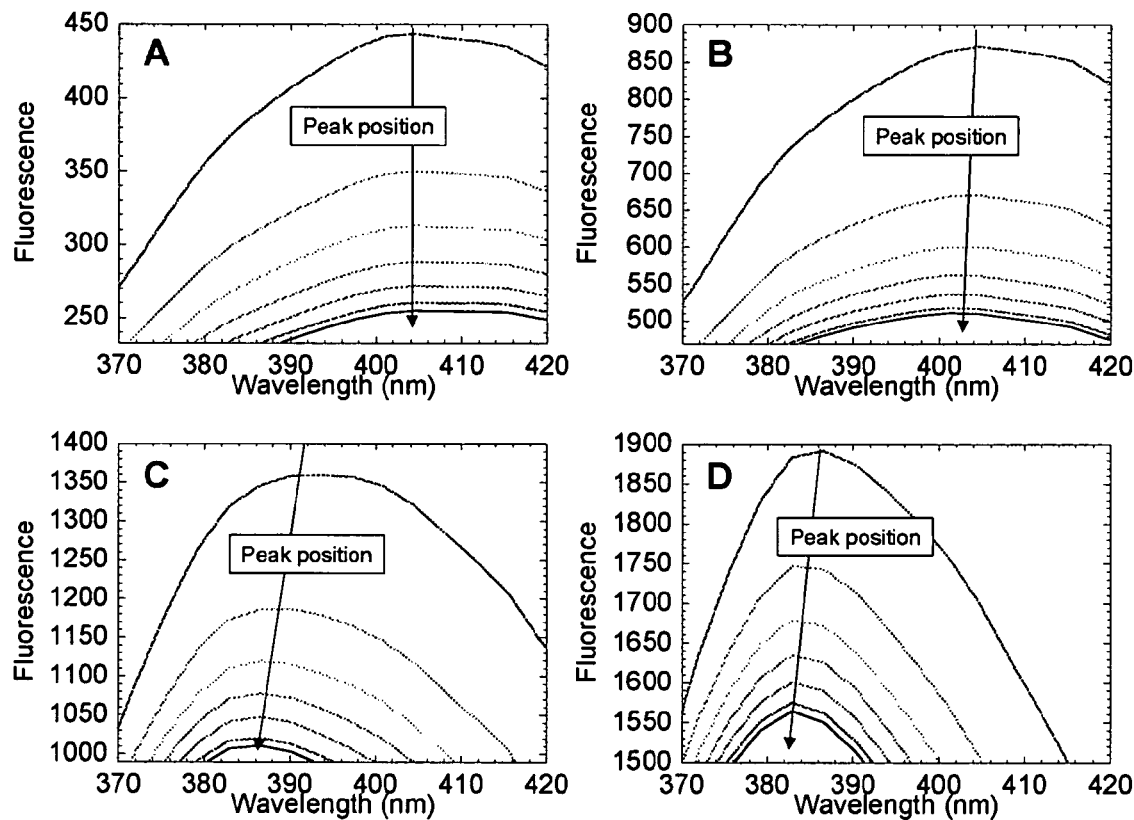
FIGS. 6A, 6B, 6C, and 6D illustrate the determination of the presence and amount of the tag based on the shifts of the fluorescence peak position during the measurement.

One of the unexpected findings of this invention is the possibility of selection of two fluorescence wavelengths so that their ratio changes differently during the measurement depending if a polymer has a tag or not. FIG. 4 illustrates this new aspect in determinations of tags. Ratio of fluorescence intensities of two properly selected fluorescence wavelengths decreases as a function of measurement time if the tag is absent in the polymer and increases if tag is present at different levels. A direct correlation between the level of the tag in the polymer and fluorescence ratio was clearly observed after 2.5 min of measurements can be seen in FIG. 5 while initially (start of measurement) there was no such correlation.

Example 3

Experimental Results Using bis(Biphenylyl)oxadiazole

Under the 355 nm excitation, the bis(Biphenylyl) oxadiazole tag has much stronger fluorescence intensity. Thus, it can be used at lower concentrations (at least 5 times less) compared to tert-butyl phenyl oxadiazole. For comparison of the fluorescence intensities, the amount of excitation light was reduced compared to the measurements with tert-butyl phenyl oxadiazole.

Figure 7:
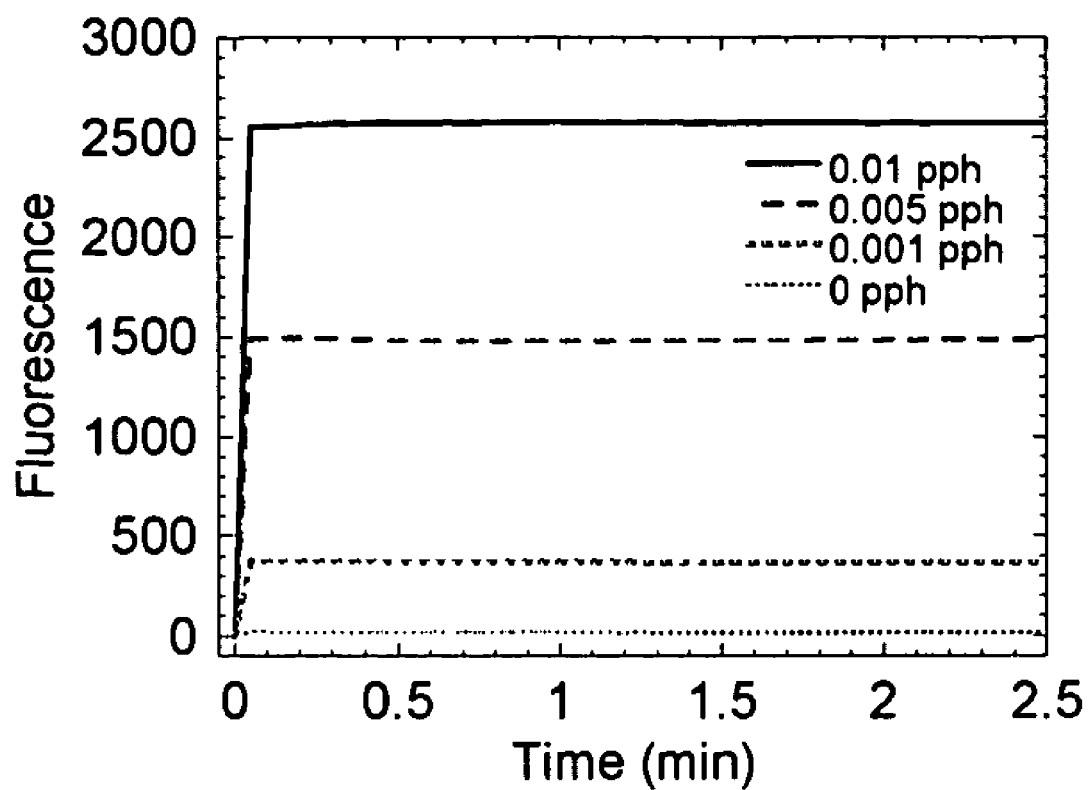
FIG. 7 illustrates the time-dependent fluorescence intensity at 386 nm of samples with different concentrations of bis(biphenyl)oxadiazole in polycarbonate.
Figure 8:
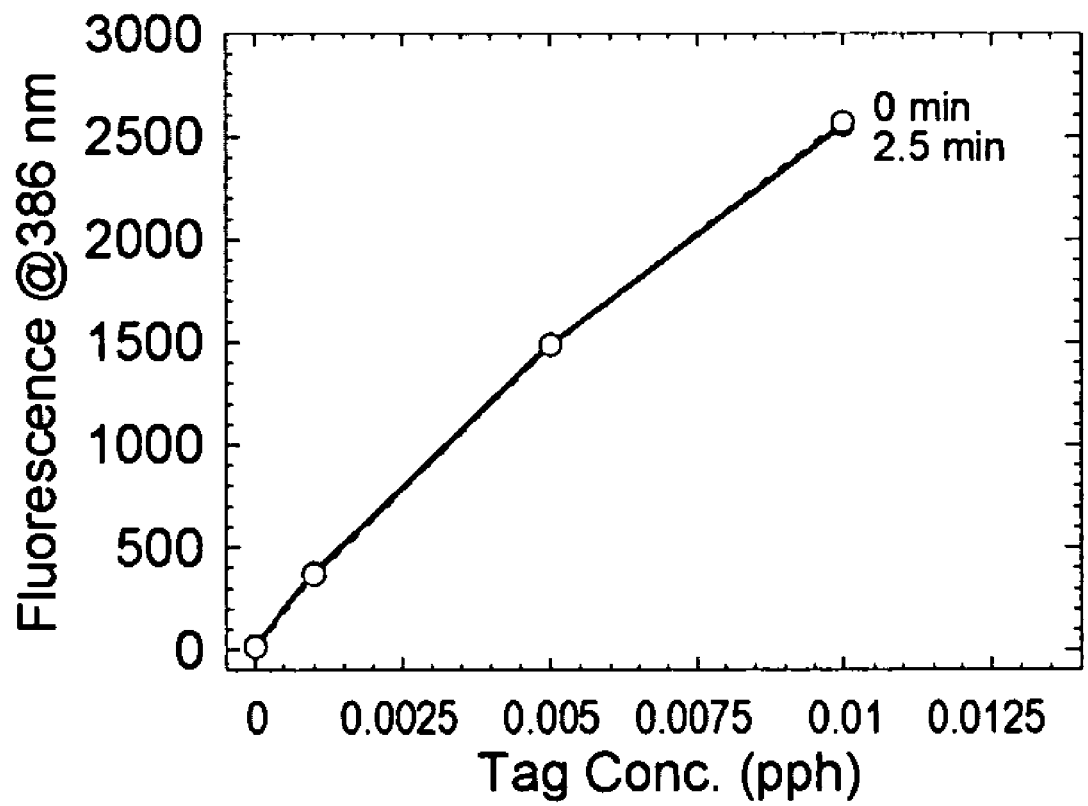
FIG. 8 is a graphical representation of the time-dependent fluorescence intensity at 386 nm of samples with different levels of bis(biphenyl)oxadiazole incorporated into polycarbonate.
Figure 9:
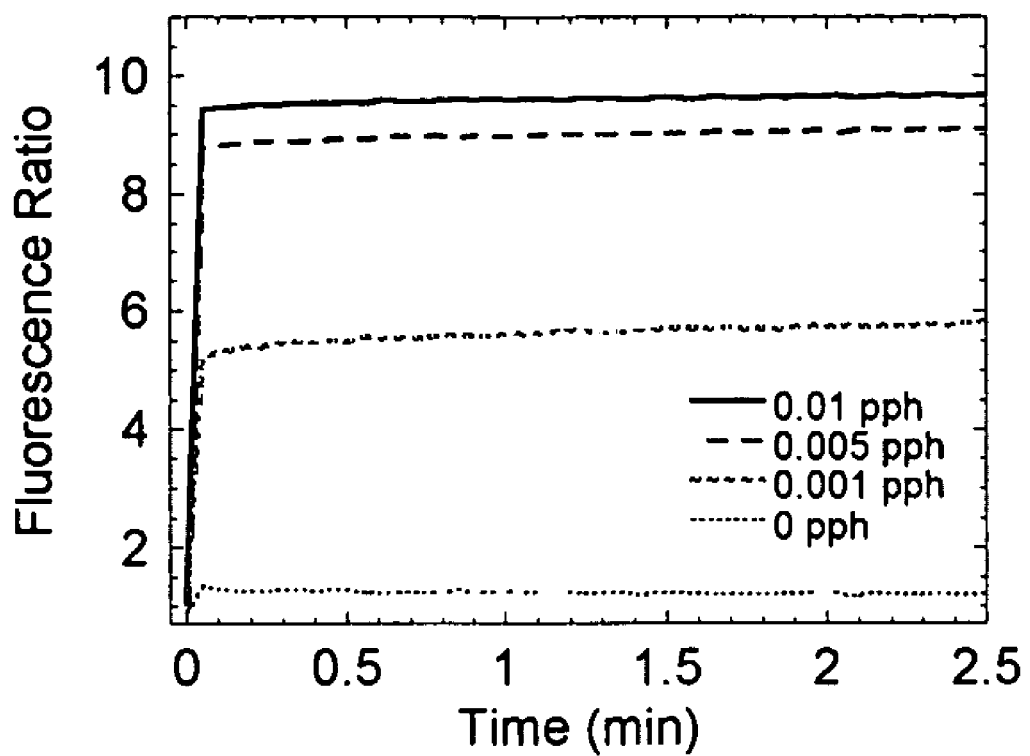
FIG. 9 is a graphical illustration of the ratio of fluorescence intensities of two selected fluorescence wavelengths as a function of measurement time for polymers with different levels of bis(biphenyl)oxadiazole.
Figure 10:
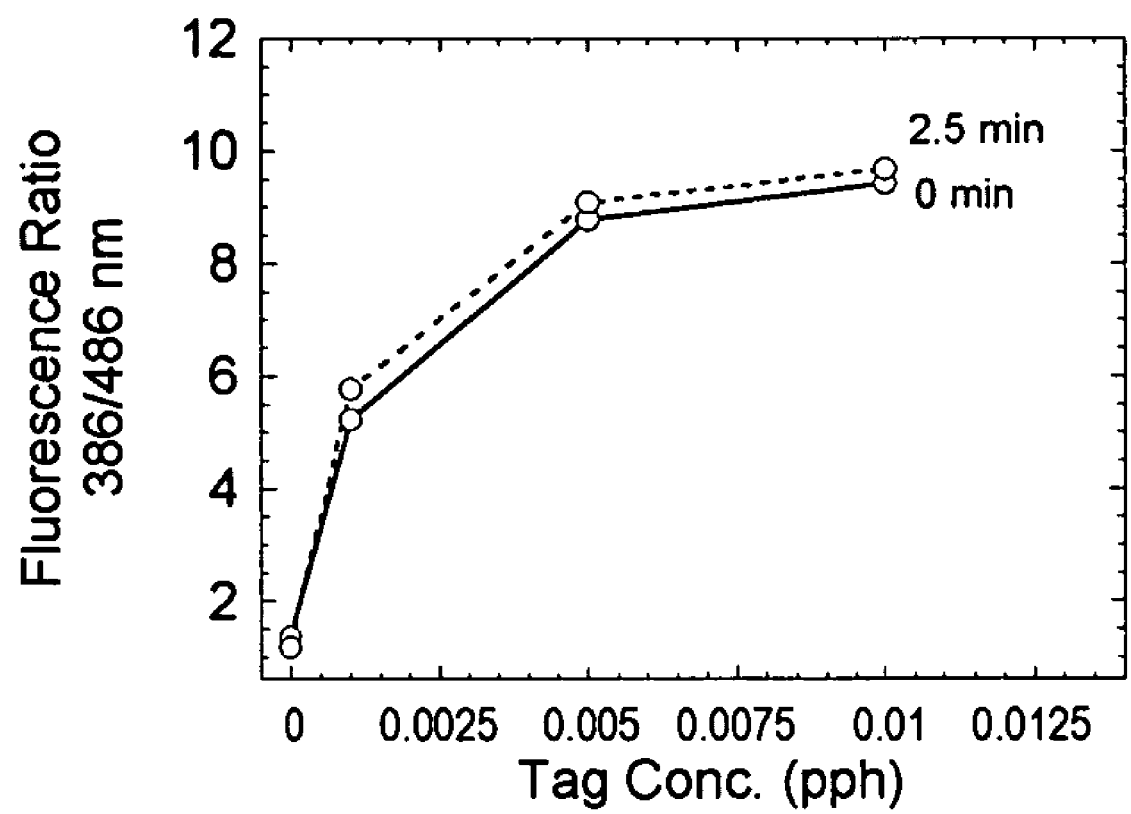
FIG. 10 is an illustration of the direct correlation between the level of bis(biphenyl)oxadiazole in the polymer and fluorescence ratio before and after 2.5 min of measurements.

The time-dependent fluorescence intensity at 386 nm of samples with different levels of the tag bis(Biphenylyl) oxadiazole incorporated into polycarbonate are presented in FIG. 7. There was no significant observed change in the time-dependent behavior of the fluorescence response. Calibration curves of fluorescence intensity at 386 nm as a function of the tag concentration in polycarbonate are presented in FIG. 8. These solid and dotted curves illustrate that the fluorescence of the tagged materials does not change during the measurements. Similarly, the fluorescence ratio does not appreciably change during 2.5 min of measurements as shown in FIGS. 9 and 10.

It is important to note that fluorescence the of the Bis (biphenylyl)oxadiazole taggant is not affected by UV radiation. This is of particular importance if the final use is an optical disc (and especially a DVD) that will be exposed to a strong UV dose as part of the adhesive curing process (bonding). Compounds combining good heat stability, excellent quantum efficiency and stability of the fluorescence in PC under UV radiation are molecules of choice. The Bis(biphenylyl)oxadiazole is a good example of this category.

Figure 11:
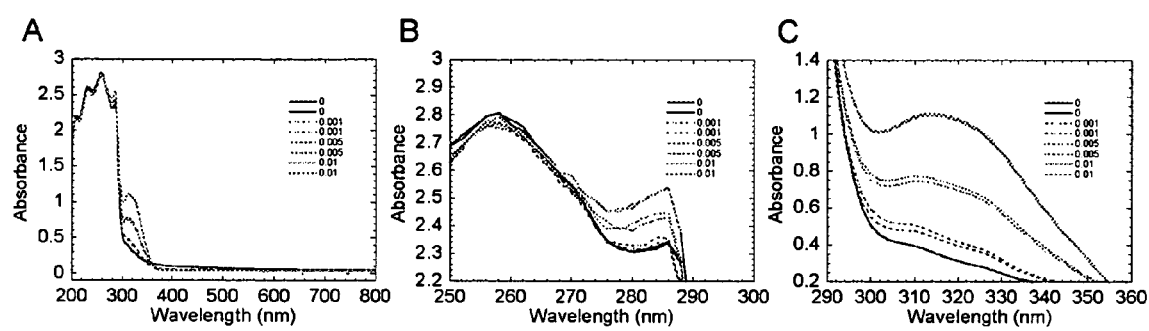
FIGS. 11A, 11B, and 11C illustrate the absorption spectra of bis(Biphenyl) oxadiazole at different concentrations and a control.
Figure 12:
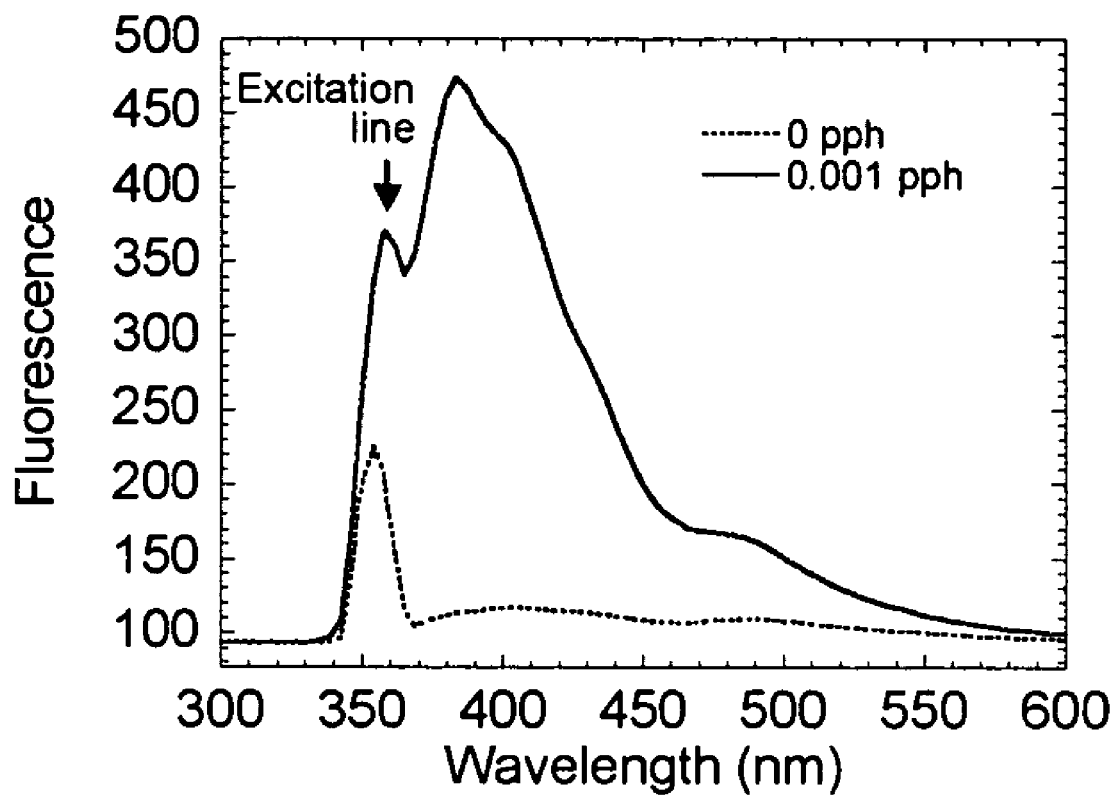
FIG. 12 is a graphical representation of a comparison of fluorescence from a tagged polymer having 0.001 pph of bis(Biphenyl) oxadiazole and a control with no bis(Biphenyl) oxadiazole.

Another aspect of this invention is that the taggant can be incorporated into the optical media article that cannot be seen by UV-Visible spectroscopy. Here the taggant absorption is "hidden" behind the polycarbonate absorption, which is important for antipiracy purposes. FIG. 11 demonstrates the absorption spectra of bis(Biphenylyl) oxadiazole and a control DVD. This figure illustrates that the absorption features of bis(Biphenylyl) oxadiazole at 0.001 pph concentration in the polymer are almost hidden by the absorbance of polymer. Importantly, as seen in FIG. 12, fluorescence signal from the polymer with only 0.001 pph of bis(Biphenylyl) oxadiazole is at least 10 times stronger than the fluorescence of polymer itself. Thus, the concentration of the taggant can be reduced significantly and its absorbance will be completely hidden in the absorption profile of the polycarbonate.

The methods and articles disclosed herein provide a method of authenticating useful in the authentication and confirmation of the source and identify of polymer-based substrates, especially polycarbonate based materials and of articles made from such substrates.

The presence of optically variable tag in a particular substrate or data storage media provides for a variety of options with respect to a particularly selected authentication signal for an authenticatable polymer. As a result, counterfeiters and illegitimate producers and sellers will find it more difficult to 'mimic' the authentication signal for an authenticatable polymer and articles legitimately made therefrom. Moreover, in one exemplary embodiment, the optically variable tags used herein are 'hidden' behind the absorption of the substrate polymer, for example, when the substrate polymer is polycarbonate. In another embodiment, the fluorescence of the optically variable tags is unaffected by UV radiation. This is particularly advantageous if the authenticatable polymer is used in a formed article that is exposed to strong UV light as part of a manufacturing process such as adhesive curing or bonding. By using a 'hidden' optically variable tag, counterfeiters and illegitimate producers and sellers may be more readily identified and apprehended.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of authenticating that a test polymer is an authenticatable polymer, wherein the authenticatable polymer has an authentication signal and comprises a substrate polymer and an optically variable tag, the optically variable tag having a fluorescence emission whose wavelength and/or intensity change over time, the method comprising
   subjecting the test polymer to a stimulus sufficient to cause fluorescence of the optically variable tag,
   determining a test signal from the fluorescence of the test polymer, and
   authenticating that the test polymer is an authenticatable polymer if the test signal is the same as the authentication signal of the authenticatable polymer.

2. The method of claim 1 wherein the wavelength and intensity of the fluorescence emission changes over time.

3. The method of claim 1 wherein the optically variable tag comprises an oxadiazole derivative.

4. The method of claim 3 wherein the optically variable tag comprises at least one of tert-butyl phenyl oxadiazole, bis(Biphenylyl) oxadiazole, and combinations of the foregoing optically variable tags.

5. The method of claim 1 wherein the optically variable tag has a first peak position of about 160 to about 1100 nm and a second peak position that is shifted from the first peak position by about 2 to about 300 nm.

6. The method of claim 5 wherein the optically variable tag has a first peak position of about 250 to about 750 nm and a second peak position that is shifted from the first peak position by about 5 to about 200 nm.

7. The method of claim 6 wherein the optically variable tag has a first peak position of about 300 to about 700 nm and a second peak position that is shifted from the first peak position by about 10 to about 100 nm.

8. The method of claim 1 wherein the optically variable tag is present in the authenticatable polymer in an amount of no more than or equal to about 2% by weight, based on the total weight of the authenticatable polymer.

9. The method of claim 1 wherein the optically variable tag is present in the authenticatable polymer in an amount greater than or equal to about $10^{-18}$ weight percent, based on the total weight of the authenticatable polymer.

10. The method of claim 9 wherein the optically variable tag is present in the authenticatable polymer in an amount greater than or equal to about $10^{-12}$ weight percent, based on the total weight of the authenticatable polymer.

11. The method of claim 10 wherein the optically variable tag is present in the authenticatable polymer in an amount greater than or equal to about $10^{-6}$ weight percent, based on the total weight of the authenticatable polymer.

12. The method of claim 1 wherein the optically variable tag is present in the authenticatable polymer in an amount of at least 0.0001 weight percent, based on the total weight of the authenticatable polymer.

13. The method of claim 12 wherein the optically variable tag is present in the authenticatable polymer in an amount of about 0.0001 to about 0.05 weight percent, based on the total weight of the authenticatable polymer.

14. The method of claim 1 wherein the substrate polymer is polycarbonate.

15. The method of claim 1 wherein the test signal is at least one selected from the group consisting of intensity of fluorescence, shape of a fluorescence peak, location of a fluorescence peak, duration or decay of fluorescence over time or after removal of a heat source, the ratio of fluorescence intensity at least two different wavelengths and combinations thereof.

16. The method of claim 1 wherein the test signal is a ratio of the fluorescence intensity.

17. A method of making an authenticatable article comprising:
    incorporating together a substrate polymer and an optically variable tag to make an authenticatable polymer, wherein the optically variable tag has a fluorescence emission having a wavelength and/or intensity that changes over time; and
    forming an authenticatable article from the authenticatable polymer by
        melting the authenticatable polymer; and
        extruding or injection molding the authenticatable polymer;
    wherein the authenticatable article is an optical disk.

18. The method of claim 17 wherein the optical disk comprises a single plastic substrate.

19. The method of claim 17 wherein the optical disk comprises more than one substrate.

20. The method of claim 19 wherein the optical disk comprises more than one substrate and wherein the read substrate is made from an authenticatable polymer.

21. An authenticatable article made by the method comprising:
    incorporating together a substrate polymer and an optically variable tag to make an authenticatable polymer, wherein the optically variable tag has a fluorescence emission having a wavelength and/or intensity that changes over time; and
    forming an authenticatable article from the authenticatable polymer, wherein the authenticatable article is an optical disk.

* * * * *